United States Patent
Woodring et al.

(10) Patent No.: US 6,543,449 B1
(45) Date of Patent: Apr. 8, 2003

(54) MEDICAL VENTILATOR

(75) Inventors: Paul L. Woodring, Del Mar, CA (US); Gardner J. Kimm, Carlsbad, CA (US); Robert L. Stephenson, Carlsbad, CA (US); David R. Rogers, Solana Beach, CA (US); Donald J. Novkov, Encinitas, CA (US); Rebecca A. Mabry, Rancho Santo Margarita, CA (US); Steve Harrington, Cardiff, CA (US)

(73) Assignee: Respironics, Inc.

( * ) Notice: Subject to any disclaimer, the term of this patent is extended or adjusted under 35 U.S.C. 154(b) by 0 days.

(21) Appl. No.: 09/156,463

(22) Filed: Sep. 18, 1998

Related U.S. Application Data

(60) Provisional application No. 60/059,676, filed on Sep. 19, 1997.

(51) Int. Cl.$^7$ .............................................. A61M 16/00
(52) U.S. Cl. ........................... 128/204.18; 128/204.21; 128/205.23
(58) Field of Search ...................... 128/204.18, 204.21, 128/204.23, 205.23

(56) References Cited

U.S. PATENT DOCUMENTS

| | | | | |
|---|---|---|---|---|
| 3,250,458 A | | 5/1966 | Caldwell .................... 230/129 |
| 3,676,013 A | | 7/1972 | Albertson ................... 415/128 |
| 3,976,064 A | * | 8/1976 | Wood et al. ............ 128/204.21 |
| 4,206,754 A | * | 6/1980 | Cox et al. ............... 128/204.26 |
| 4,323,064 A | * | 4/1982 | Hoenig et al. ......... 128/204.21 |
| 4,345,612 A | * | 8/1982 | Koni et al. ............. 128/204.21 |
| 4,380,233 A | * | 4/1983 | Caillot .................. 128/204.21 |
| 4,579,115 A | * | 4/1986 | Wallroth et al. ....... 128/204.21 |
| 4,584,996 A | * | 4/1986 | Blum .................... 128/204.21 |
| 4,637,385 A | * | 1/1987 | Rusz ..................... 128/204.21 |
| 4,867,152 A | * | 9/1989 | Kou et al. ............. 128/204.21 |
| 4,905,688 A | * | 3/1990 | Vicenzi et al. ......... 128/204.21 |
| 4,938,661 A | | 7/1990 | Kobayashi et al. ...... 415/199.1 |
| 4,957,107 A | | 9/1990 | Sipin .................... 128/204.21 |
| 5,117,819 A | * | 6/1992 | Servidio et al. ........ 128/204.18 |
| 5,211,170 A | | 5/1993 | Press .................... 128/204.18 |
| 5,231,981 A | | 8/1993 | Schreiber et al. ...... 128/205.23 |
| 5,320,489 A | | 6/1994 | McKenna ................ 415/208.3 |
| 5,495,077 A | | 2/1996 | Miller et al. | |
| 5,537,997 A | | 7/1996 | Mechlenburg et al. | |
| 5,660,171 A | | 8/1997 | Kimm et al. | |
| 5,678,539 A | | 10/1997 | Schubert et al. ....... 128/204.21 |
| 5,694,926 A | | 12/1997 | DeVries et al. | |

FOREIGN PATENT DOCUMENTS

| | | |
|---|---|---|
| WO | WO 98/41267 | 9/1998 |
| WO | WO 98/41269 | 9/1998 |
| WO | WO 98/41270 | 9/1998 |
| WO | WO 98/41271 | 9/1998 |

* cited by examiner

Primary Examiner—Aaron J. Lewis
(74) Attorney, Agent, or Firm—Troutman Sanders LLP; Gerald R. Boss; Ryan A. Schneider

(57) ABSTRACT

A ventilatory system which may be operated in an invasive and a non-invasive mode is provided utilizing a graphical user interface for presenting only those controlled parameters utilized for that specific mode of operation. Volume and pressure ventilatory support parameters are included for invasive ventilation and non-invasive ventilation control parameters are provided for non-invasive ventilatory assistance. The graphical user interface enables an operator to select the desired mode of operation wherein only those parameters related to that specific mode of operation are presented. Furthermore, a blower is provided for providing an air source to the ventilator enabling the ventilator to be self sufficient.

29 Claims, 20 Drawing Sheets

FIG A

| Setting | Range | Units |
|---|---|---|
| Ventilation Type | Volume, Pressure, Non-Invasive | none |
| Mode (Volume Ventilation) | A/C, SIMV, CPAP | none |
| Mode (Pressure Control Ventilation) | A/C, SIMV, CPAP | none |
| Mode (Noninvasive Ventilation) | Spont/Timed, Spont | none |
| Apnea Interval | 10 - 60 | seconds |
| Apnea Rate | 1 - 80 | Bpm |
| Wave Form | Square, Ramp | none |
| Peak Flow | 3 - 140 | Lpm |
| Tidal Volume | 50 - 2500 | ml |
| Respiratory Rate | 1 - 80 | Bpm |
| Plateau | 0.0 - 2.0 | seconds |
| Pressure Sensitivity | 0.1 - 20.0 | $cmH_2O$ |
| E-Trigger | 10 - 45 | % Peak Flow |
| PEEP/CPAP | 0 - 35 | $cmH_2O$ |
| Pressure Support (PSV) | 0 - 100 | $cmH_2O$ |
| Risetime | 0.1 to 0.9 | seconds |
| O2% | 21 - 100 | % Oxygen |
| IPAP | 2 - 35 | $cmH_2O$ |
| EPAP | 2 - 25 | $cmH_2O$ |
| I-Time | .1 to 9.9 | seconds |
| Pressure Control | 5 to 100 | $cmH_2O$ |
| Patient Type | Adult, Pediatric | |

FIG 22

MEDICAL VENTILATOR

This application claims priority of provisional application Ser. No. 60/059,676 filed on Sep. 19, 1997.

BACKGROUND OF THE INVENTION

1. Field of Invention.

This invention relates generally to a medical ventilator and more particularly to a medical ventilator which is operable in both an invasive and non-invasive ventilatory environment.

2. Description of the Related Art.

Ventilators are used by patients in various health situations. Typically, these patients have weak physiological attributes that prevent them from breathing unassisted and require invasive ventilation. Invasive ventilatory support generally requires the patient having either a tracheotomy or endotracheal tube disposed into the trachea of the patient. Such treatment generally occurs in hospitals and is administered in acute care situations or post operative recovery situations. Ventilators, such as the Siemens 300, are known to provide invasive ventilatory assistance.

The use of invasive ventilatory support has many risks. By positioning an endotracheal tube down the trachea of a patient, the patient is placed at some medical risk. Typically, there are certain physiological attributes in the trachea of a person for preventing bacteria and the like from invading into a person's lung. However, the endotracheal tube circumvents these natural defense systems. Accordingly, patients may acquire pneumonia by having the bacteria circumvent the natural defense mechanism of the body. Additionally, positioning of an endotracheal tube into a patient subjects the patient to a risk of tracheal abrasion. Overall, the positioning of an endotracheal tube, known as intubation, should be avoided when necessary.

Typically, when a patient is placed on ventilatory support, most patients are subsequently weaned from the ventilator. Weaning involves manipulating the ventilator from that mode when the ventilator provides the most ventilatory assistance to the mode when the patient is providing most of the breathing. However, during the weaning of the patient from the ventilator, the patient remains intubated continuing further exposing the patient to health risks. Thus, there is a need for a medical ventilator that will enable a patient to be extubated, having the endotracheal tube removed from the trachea, as soon as possible to eliminate health risks.

Additionally, there are situations which arise wherein a patient having difficulty breathing is intubated prematurely and connected to a ventilator. This generally occurs since the attending physician lacks a ventilatory device which can provide ventilation in a non-invasive environment for initially determining if the patient is merely having difficulty breathing or truly requires invasive ventilation. This situation arises due to the costs associated with having a separate invasive ventilator and a non-invasive respirator which may be utilized to provide the patient with initial ventilation support. Due to the costs and expenses of having duplicate machines, most hospitals merely have invasive ventilators at their disposal.

Also, to provide ventilatory assistance in hospitals, the hospitals generally have specially designed respiratory care facilities having compressed air and oxygen hookups permanently affixed in a specific location. Such fully equipped facilities are expensive and also limit the areas where the ventilator may be accessed. Consequently, some patients who are otherwise healthy but require invasive ventilation are prevented from discharge due to their dependency on the respiratory care facility. With the high cost of hospital stays, some patients who require long term ventilatory utilization may occur exceptional hospitalization charges for the use of such expensive facilities. Thus, it is desirous to enable the ventilatory patient to be discharged to a low-acuity subacute facility or nursing home if the situation is warranted. However, most of these facilities lack the necessary pressurized air and oxygen hookups thus preventing the ventilatory patient from being discharged.

Also, since surgical areas and emergency room areas are typically stressful environments, it is desired that ventilators are easy to operate. This is also essential in today's health care environment since many different type of health care providers are assisting patients. These include respiratory therapists, nurses and physicians. Accordingly, it is desired that an intuitive ventilator exists for both invasive and non-invasive ventilation.

SUMMARY

Accordingly, it is an object of the present invention to provide a ventilator that can be used in both an invasive and non-invasive environment.

Furthermore, it is an object of the present invention to provide a ventilator which can operate in both an invasive and non-invasive environment and having an operator interface that is simple to use for reducing error in operation;

Also, it is an object of the present invention to provide a self contained invasive/non-invasive ventilator having its own source of air and having the ability to mix with an oxygen or other gas source to provide flexibility in providing ventilatory assistance at different physical locations without requiring special respiratory care facilities with preexisting air sources.

The above objectives are accomplished according to the present invention by providing a ventilatory system for use in an invasive and non-invasive ventilator environment. The ventilator system includes a gas flow generator for providing a flow of gas to a patient. A conduit delivers the gas flow to the airway of the patient. At least a first valve regulates the delivery of the gas from the gas flow generator to the conduit. A controller controls the delivery of the gas flow to the patient. The system further includes a first set of operational parameters for directing the controller to control the delivery of gas to a patient if the patient is being ventilated in an invasive ventilation mode and a second set of operational parameters for directing the controller to control the delivery of gas to the patient if the patient is being ventilated in a non-invasive ventilation mode. Also a selector is utilized for selecting either the first or second set of parameters to direct the ventilator to provide either invasive or non-invasive ventilatory support to the patient.

Also, a unique blower is utilized for providing ventilatory assistance. The blower is a multi-stage centrifugal blower having an air inlet for receiving air from the ambient environment. A first impeller imparts centrifugal force onto the air. A first stator receives the air from the impeller and pressurizes the air. A second impeller subsequently receives the air from the first stator and imparts additional centrifugal force onto the air. A first impeller spacer directs the air from the first stator to the second impeller. A second stator receives the air from the second impeller and further pressurizes the air. A third impeller receives the air from the second stator and further imparts centrifugal force into the air. A second impeller spacer directs the air from the second stator to the third impeller. A blower outlet permits the pressurized air to leave the blower assembly. The overall impeller and stator configuration enables air to be pressurized to at least one hundred and sixty centimeters $H_2O$ when exiting the blower outlet.

Also, a graphical user interface is utilized in the ventilator for controlling the operation of the ventilator. An activation area is present for displaying a first activation device for a first mode of ventilation and a second activation device for a second mode of ventilation. A selector selects either the first or second activation device. A display area then displays the operational parameters pertaining either to the first or second mode of ventilation depending on the mode selected by the operator. Only those operational parameters relating to the particular ventilation mode selected by the operator are displayed.

These and other objects, features, and characteristics of the present invention, and the combination of parts and economies of manufacture, will become more apparent upon consideration of the following detailed description and appended claims with reference to the accompanying drawings, all of which form a part of the specification, wherein like reference numerals designate corresponding parts in the various FIGS.

DESCRIPTION OF THE DRAWINGS

The construction and design to carry out the invention will hereinafter be described together with other features thereof. The invention will be more readily understood from a reading of the following specification and by reference to the accompanying drawings forming a part thereof, wherein an example of the invention is shown and wherein:

FIG. 22 is a table of operational parameters according to the present invention;

DESCRIPTION OF THE PREFERRED EMBODIMENT

Figure 1:
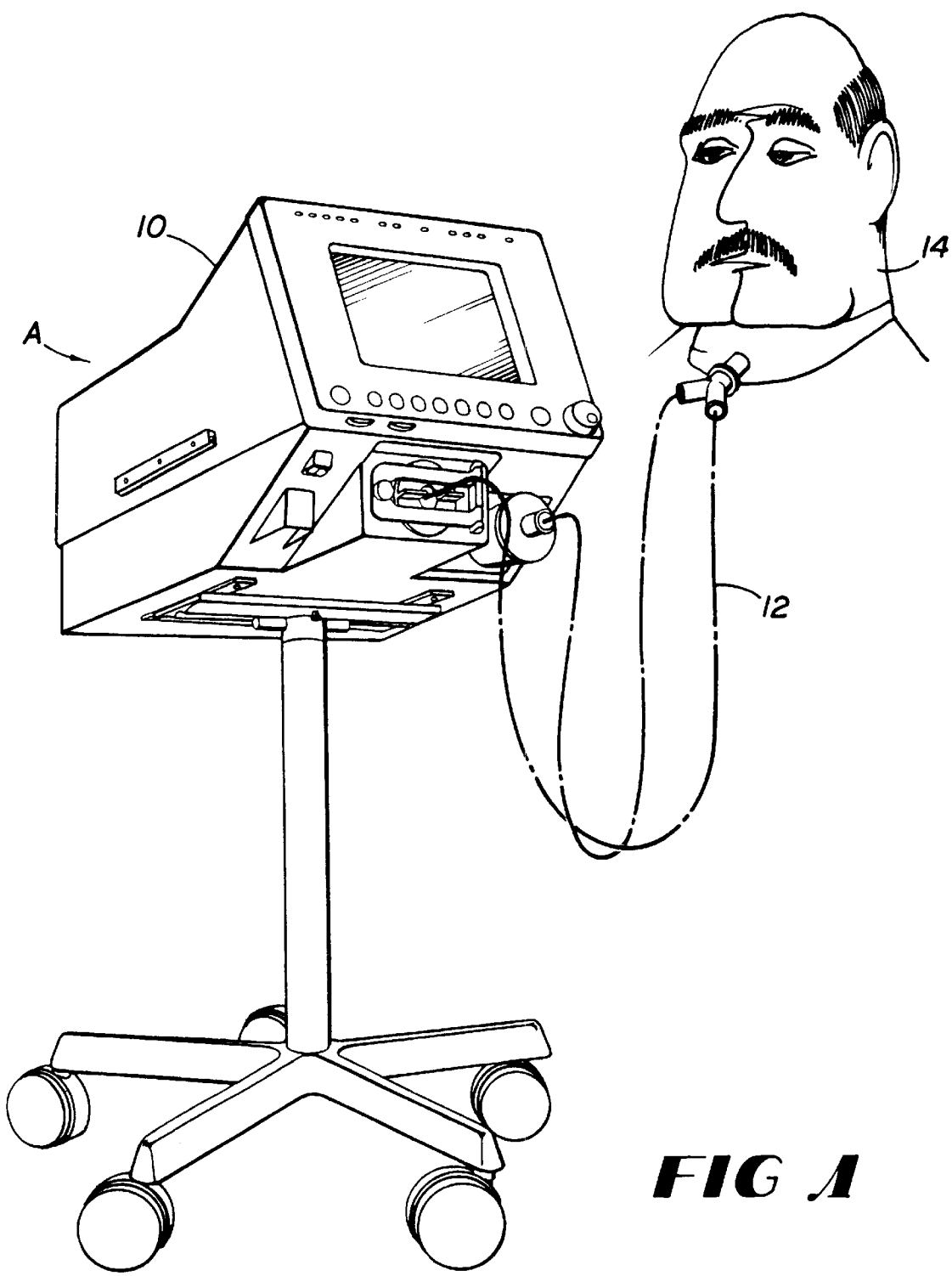
FIG. 1 is a perspective view of a ventilator according to the present invention being used in an invasive environment.
Figure 2:
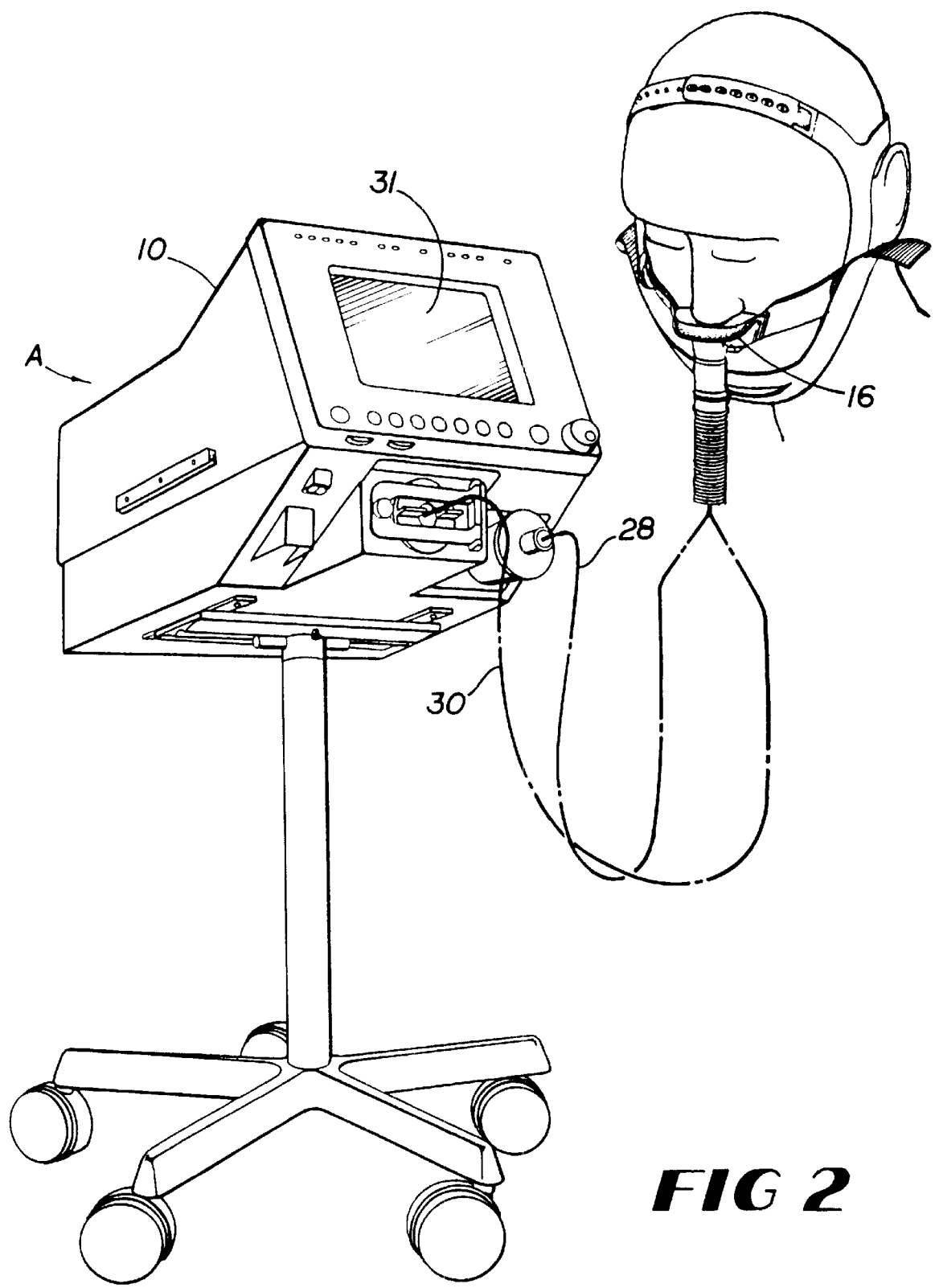
FIG. 2 is a perspective view of a ventilator according to the present invention being used in a non-invasive environment.

Referring now in more detail to the drawings, the invention will now be described in detail. As shown in FIGS. 1 and 2, respectively, invasive/non-invasive ventilator 10 provides support in both an invasive and non-invasive environment. As shown in FIG. 1, ventilatory system A includes invasive/non-invasive ventilator 10 interconnected via conduit 12 to patient 14 for providing ventilatory support in an invasive environment. Invasive ventilation includes positioning tubing directly into the trachea of a patient either through a tracheotomy or an endotracheal tube. Invasive ventilation is generally administered to patients who have great difficulty breathing on their own. FIG. 2 illustrates the delivery of non-invasive ventilatory assistance to a patient via a mask 16. Non-invasive ventilation is generally administered to patients who merely require some support in their breathing.

Figure 3:
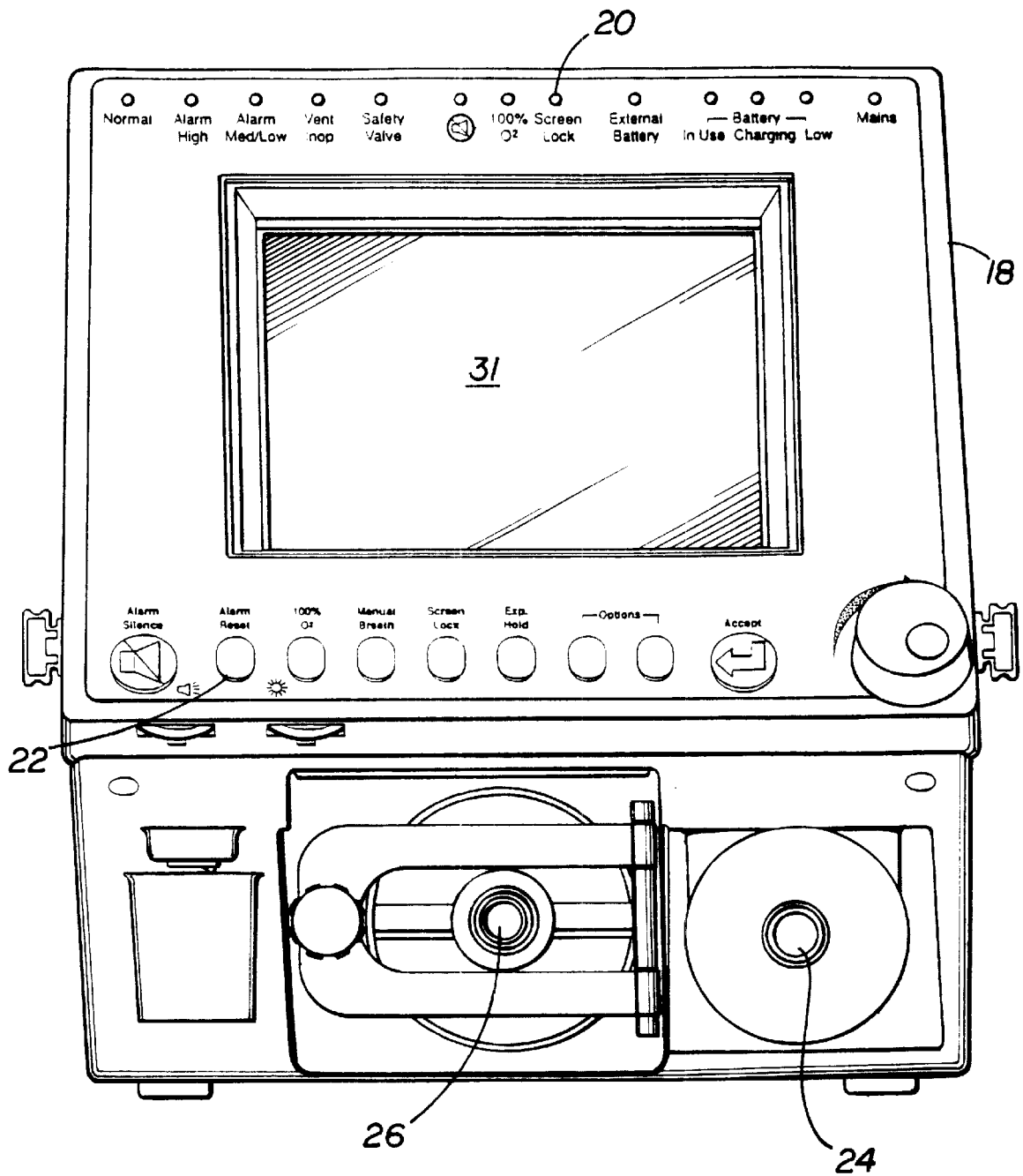
FIG. 3 is a front perspective view of an invasive/non-invasive ventilator according to the present invention.
Figure 4:
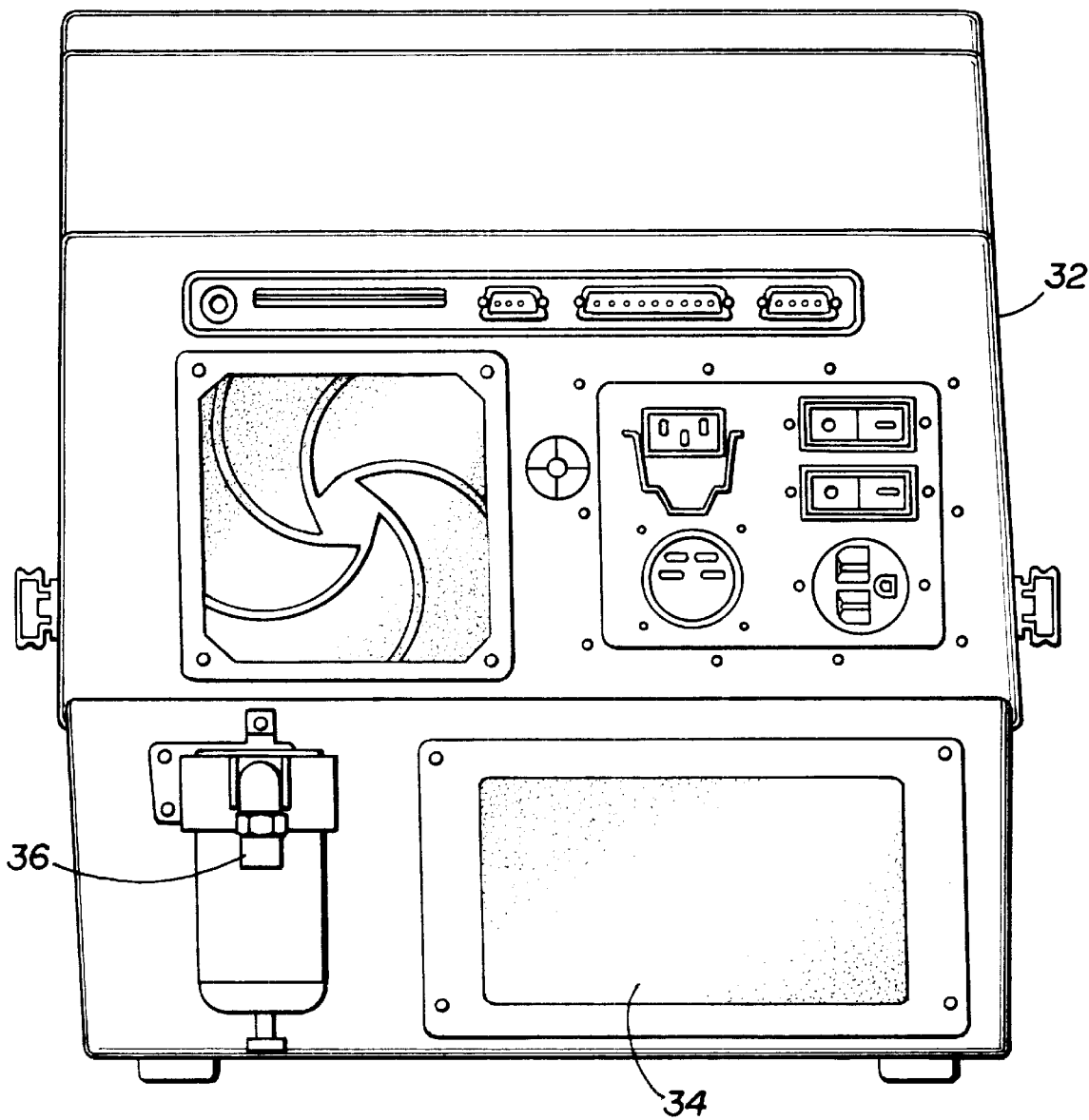
FIG. 4 is a rear perspective view of an invasive/non-invasive ventilator according to the present invention.

FIGS. 3 and 4 illustrate front and back views, respectively, of invasive/non-invasive ventilator 10. As shown in FIG. 3, front face 18 of invasive/non-invasive ventilator 10 includes a plurality of alarms 20, which are preferably light emitting diodes, or displaying various alarm conditions. These alarms include, but are not limited to, the following: high priority alarm, a medium or low alarm, the ventilator is currently inoperative, the safety valve is open, an external battery is being used or that the internal battery is either in use, charging, or low. Also located on front face 18 are control buttons 22 that enable an operator to manipulate the operation of the ventilator by simply depressing a control button. Control buttons 22 include, for example, an alarm reset, an alarm silence, a control for a manual breath, or other various options. Additionally, front face 18 includes ventilator outlet port 24 and ventilator return port 26. Conduit 12 generally consists of an inhalation passageway 28 and an exhalation passageway 30. The inhalation passageway 28 is interconnected with ventilator outlet port 24 enabling oxygen enriched air to be provided by ventilator 10 to patient 14. Exhalation air is returned through exhalation passageway 30 through ventilator return port 26 to be exhausted into the ambient environment. As shown in FIG. 4, invasive/non-invasive ventilator 10 includes back face 32. Back face 32 includes an air inlet 34 which communicates with a blower, and an oxygen inlet 36 which is selectively connectable to an oxygen source.

Figure 5:
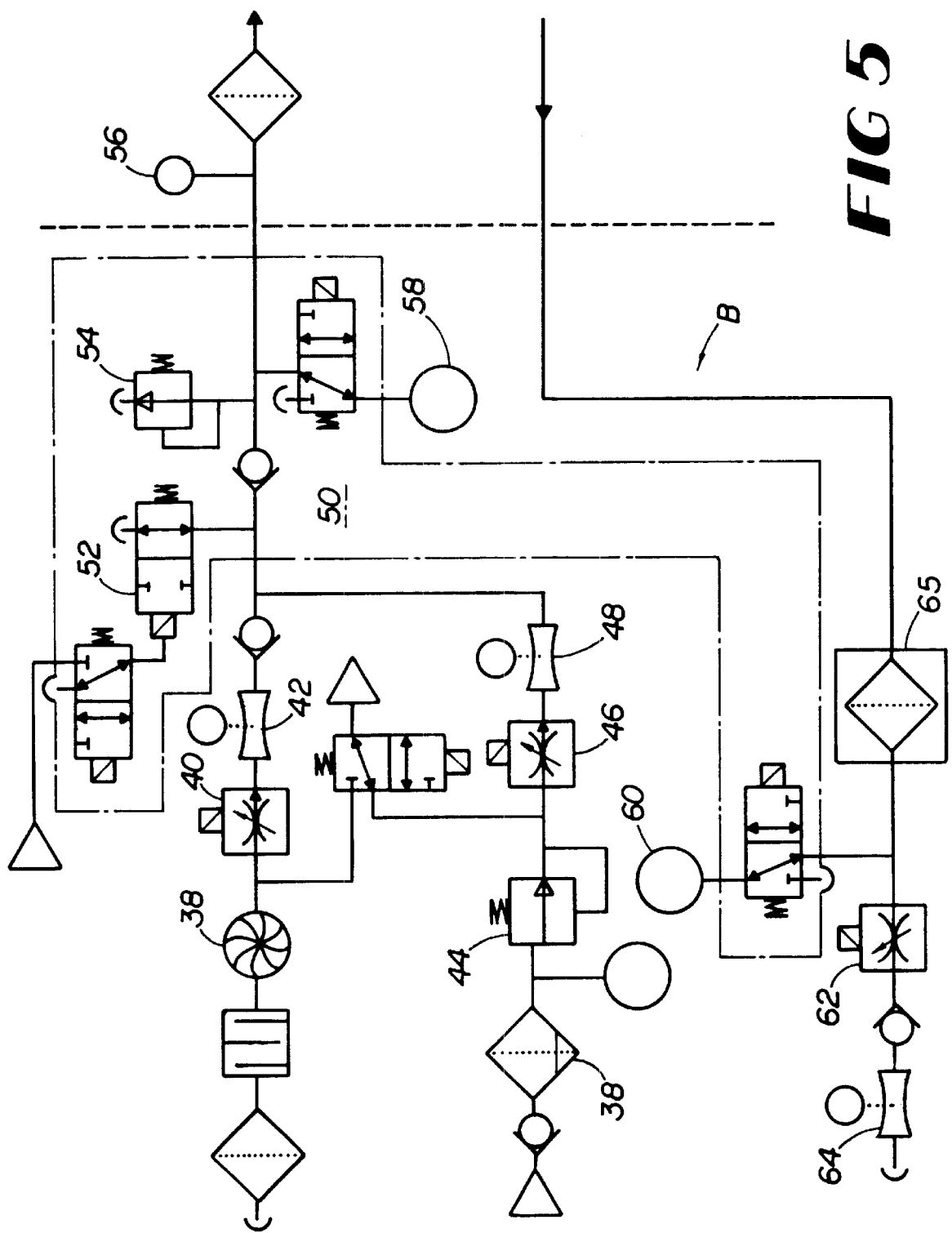
FIG. 5 is the schematic of the pneumatic components according to the present invention.

FIG. 5 illustrates the pneumatic system B of invasive/non-invasive ventilator 10. Pneumatic system B includes gas flow generator 38 that draws air from air inlet 34 for delivery to the patient. Blower valve 40 meters flow from gas flow generator 38 to achieve the proper oxygen mixture and total flow when combined with the output of the oxygen valve. Air flow sensor 42 measures the flow of air out of blower valve 40. This measurement is used for closed loop control of blower valve 40 as a means of checking the performance of blower valve 40 and as a means of checking the performance of lower valve 40. The oxygen delivery system includes an oxygen inlet 36 which connects to an oxygen supply source. Oxygen regulator 44 reduces the oxygen pressure from the inlet supply pressure and regulates it to the proper inlet pressure for oxygen flow valve 46. Oxygen flow valve 46 meters flow from oxygen regulator 44 to achieve the proper oxygen mix and total flow when combined with the output of blower valve 40. Oxygen flow sensor 48 measures the flow of oxygen out of oxygen flow valve 46. This measurement is used for closed loop control of oxygen flow valve 46 and also to compute flow/volume delivered to the patient. Inhalation manifold 50 provides a blending point for the air and oxygen flow. Safety valve 52 and pressure relief valve 54 are utilized for assisting in the safety of the patient. Safety valve 52 allows the patient to inspire ambient air when the ventilator enters the safe state. Pressure relief valve 54 provides a means of preventing excessive pressures in the system. Oxygen sensor 56 provides a measurement of the oxygen concentration of gas being blended by the oxygen and blower valves. The inhalation pressure transducer 58 provides a measurement of the patient's circuit pressure from the inhalation side of the patient's circuit. It is also utilized for detecting of patient circuit occlusions that may occur.

The exhalation system of pneumatic system B returns exhaled air from the patient to the ambient environment. The exhalation system includes exhalation pressure transducer 60, which provides a measurement of the patient circuit pressure on the exhalation side of the patient circuit. The exhalation pressure transducer may be the primary transducer used for the measurement of patient pressure data, such as peak inhalation pressure, mean airway pressure, and end inhalation pressure. Also, exhalation pressure transducer 60 is utilized for closed loop control of the exhalation valve in controlling PEEP and EPAP. Along with inhalation pressure transducer 58, exhalation pressure transducer 60 is also utilized for detection of patient circuit occlusions. Exhalation valve 62 is utilized to control venting of exhaled air to the ambient environment and to close the exhalation leg of the patient circuit during inhalation. Exhalation valve 62 also regulates patient circuit pressure to PEEP and EPAP levels. Exhalation flow sensor 64 provides a measurement of the flow leaving the ventilator. The flow includes patient exhaled gases and may include bias flow delivered by the ventilator.

Figure 19:
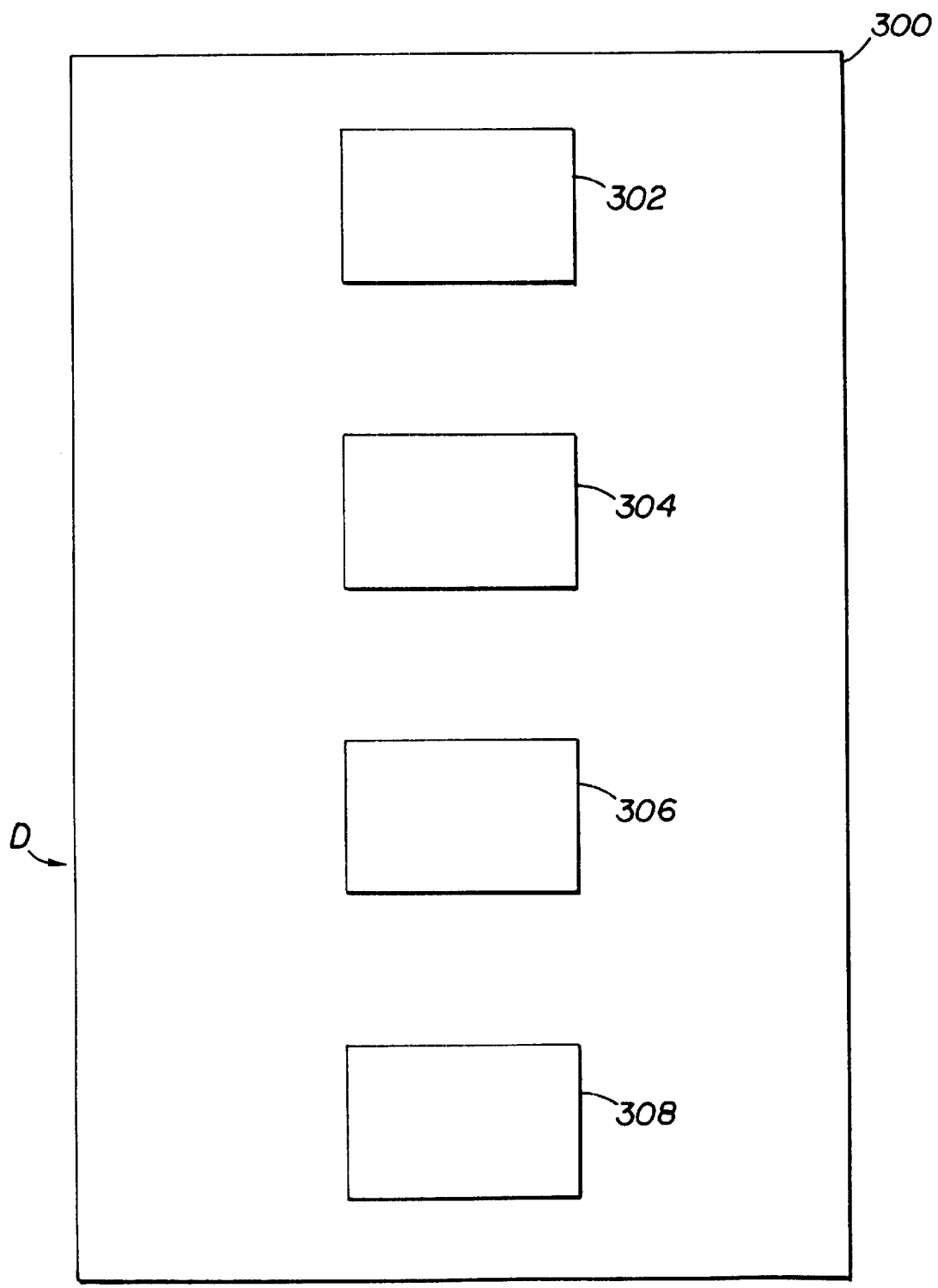
FIG. 19 is a schematic of the electronics of an invasive/non-invasive ventilator according to the present invention.

FIG. 19 illustrates controller system D. Controller system D includes a mother board 300 that provides communication between the daughter boards, power supply connector and sensor board, the cables to the oxygen valve, the air valve, and the exhalation valve, and the connection with the man-machine interface board. In one embodiment, there are seven daughter boards that connect to the mother board. These seven daughter boards include a CPU board 302, which contains a microprocessor and associated memory for storing and executing of the programs for coordination of the ventilator systems, breathing algorithms, alarms, displays and the user interface functions. Another daughter board is a digital board 304, which provides interface to the central processing unit for digital input and output signals. A third daughter board includes a VGA controller board 306, which provides control of graphical user interface 31. Gas flow generator controller board 308 controls the operation of gas flow generator 38.

Figure 6:
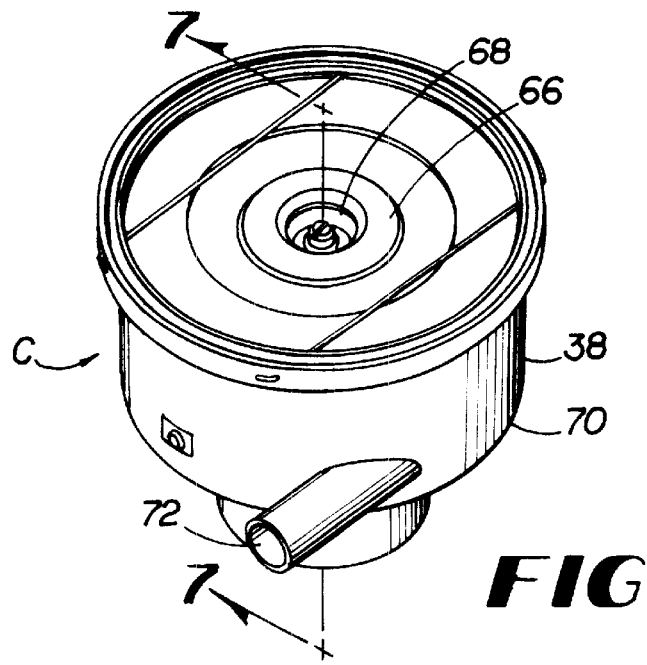
FIG. 6 is a perspective view of the blower according to the present invention.

As shown in FIGS. 6 through 18, gas flow generator 38 consists of blower assembly C. As shown in FIG. 6, blower assembly C includes an inducer 66 having a central air port 68 and a central blower housing 70 which includes an interior for housing the respective stators and impellers. A blower air outlet 72 discharges air from the blower to a conduit connected to blower valve 40.

Figure 7:
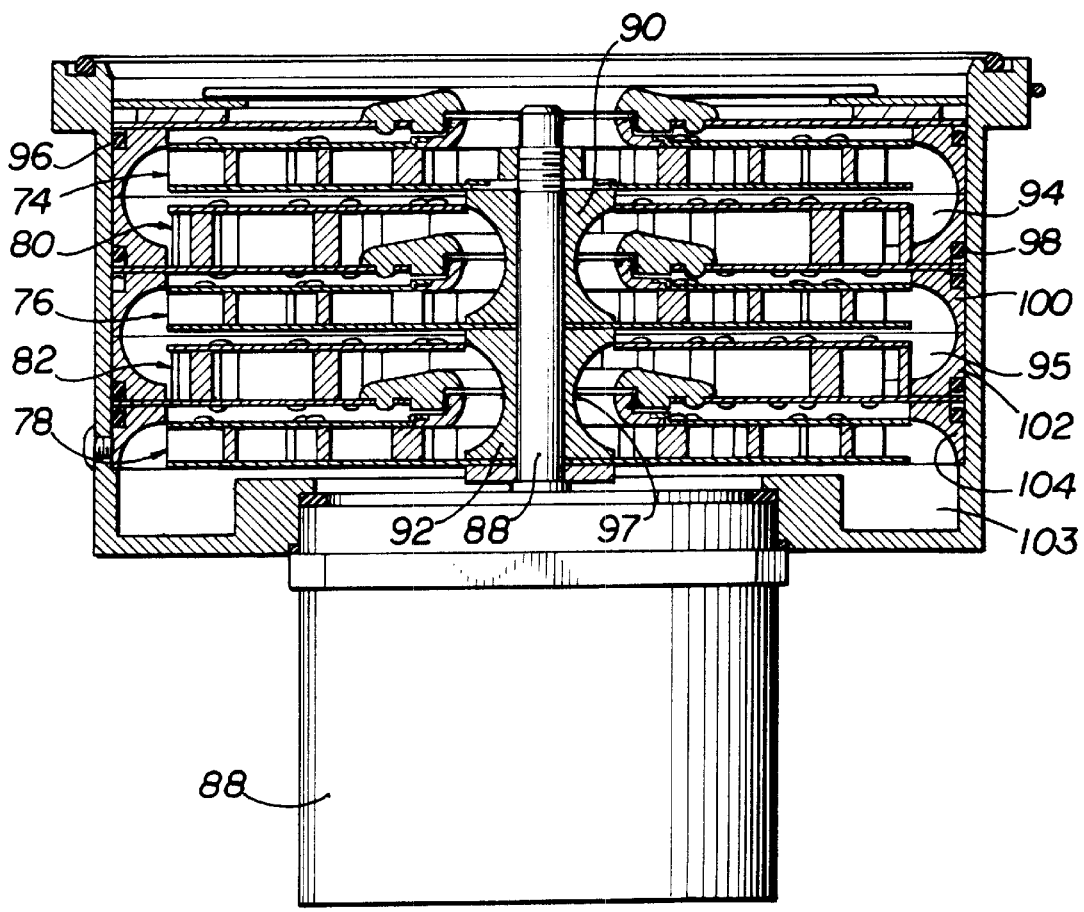
FIG. 7 is a cross-sectional view of the blower according to the present invention taken along line 7—7 of FIG. 6.
Figure 8:
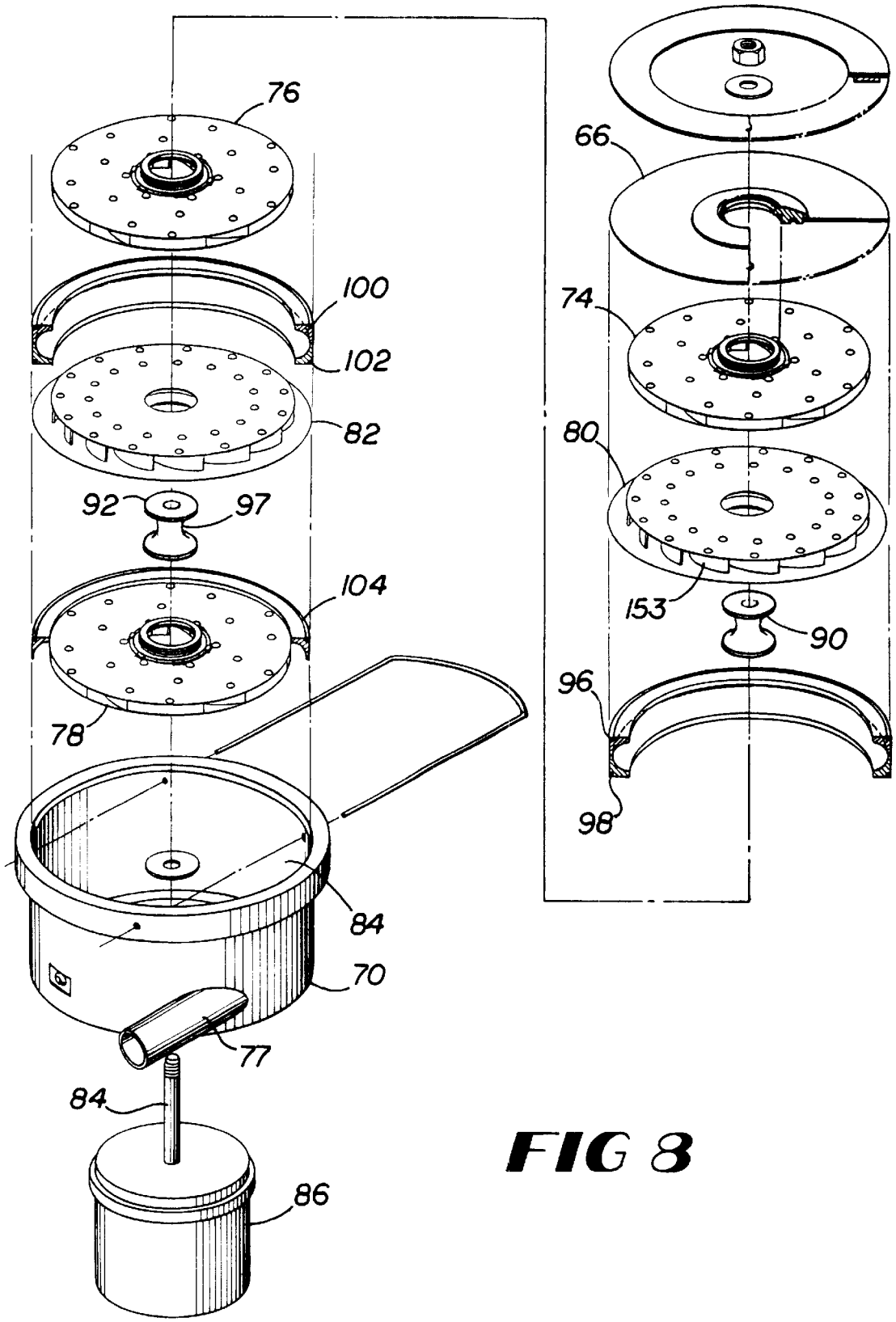
FIG. 8 is an exploded view of the blower assembly according to the present invention.
Figure 9:
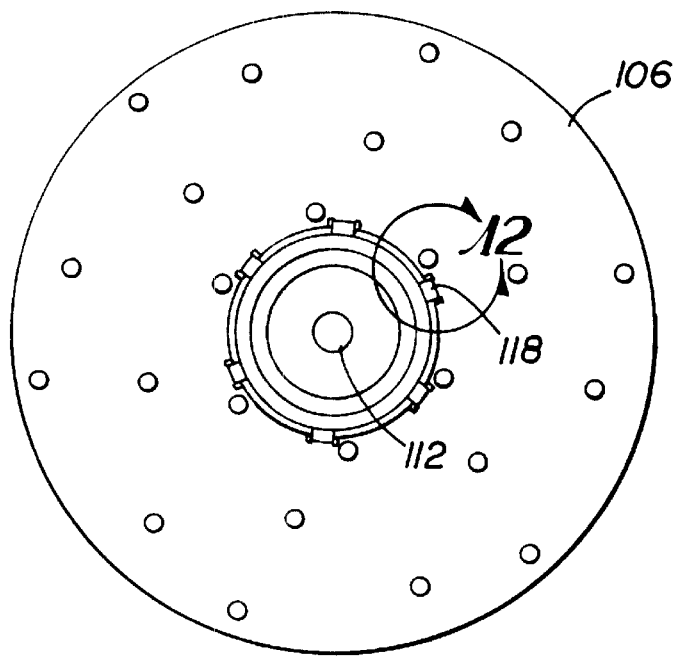
FIG. 9 is a top plain view of an impeller with a sealing ring according to the present invention.

As shown in FIGS. 7 and 8, blower assembly C is preferably a multi-centrifugal compressor. In a preferred embodiment, blower assembly C includes three rotating impellers 74, 76, and 78 and two stationary stators 80 and 82. In this configuration, the rotating impellers impart velocity onto the air that is drawn through central air port 68 through the use of centrifugal force. The air is then passed to the stationary stators wherein the velocity energy from the centrifugal force is turned into pressure energy. The multi-centrifugal compressor configuration enables the air to be manipulated by the respective impellers and stators such that sufficient pressurized air may be provided to the patient.

As shown in FIG. 8, in a preferred embodiment, blower assembly C consists of central blower housing 70 having central interior 84. A motor 86 having motor shaft 88 is utilized for rotating the respective impellers. Central blower housing 70 is generally enclosed on a bottom side having a central orifice for receiving motor shaft 88. The opposite side of central blower housing 70 is open enabling the various blower components to be positioned within central interior 84. Once the various stators and impellers are positioned within central interior 84, inducer 66 generally encloses the top of central blower housing 70 enabling air to be drawn into central interior and compressed for subsequent exit through air outlet 72.

As shown in FIGS. 7 and 8, a first impeller 74 is rotationally mounted onto motor shaft 88. First stator 80 is mounted on a first impeller spacer 90 and a second impeller 76 is mounted on first impeller spacer 90, which is then subsequently mounted on motor shaft 88. A second stator 82 is mounted on a second impeller spacer 92 and a third impeller 78 is rotationally mounted on second impeller spacer 92, which is also subsequently mounted onto motor shaft 88. First impeller 74 and first stator 80 are housed together in a first air chamber assembly 94 which is defined by stator spacers 96 and 98 which adjoin together to form an outer ring around first impeller 74 and first stator 80. Second stator spacer 100 and 102 are joined together to form a ring around the combination of second impeller 76 and second stator 82 defining a second air chamber assembly 95. Third stator spacer 104 forms a ring around third impeller 78 and in combination with blower housing 70, directs air into diffuser chamber 103 and out of the blower air outlet 72. Both first impeller spacer 90 and second impeller spacer 92 have curved interior portions 97, preferably having a radius of curvature of nine point three millimeters.

Figure 10:
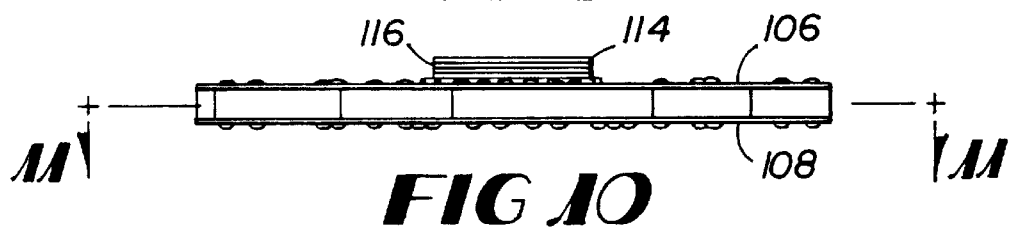
FIG. 10 is a side view of an impeller with a sealing ring according to the present invention.
Figure 13:
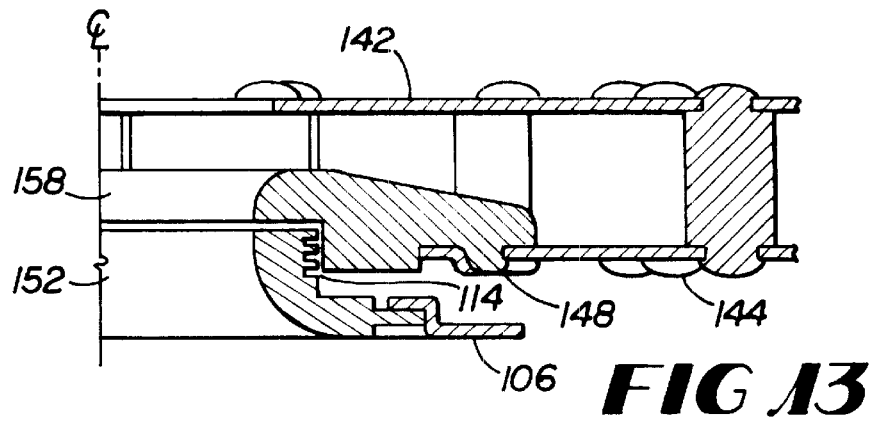
FIG. 13 illustrates the interface between an impeller and the stator of the blower according to the present invention.

FIGS. 9 through 14 illustrate the impeller assemblies 74, 76, and 78. Each respective impeller includes a top plate 106, an impeller bottom plate 108 and a plurality of impeller vanes 110. An impeller port 112 is disposed concentrically from impeller top plate 106 to impeller bottom plate 108. Labyrinth seal 114 extends upward from impeller top plate 106 to a general height. As shown in FIG. 13, labyrinth seal 114 includes a plurality of grooves for sealing engagement of the respective impellers with the respective stator. The elevated height of the grooves is shown in FIG. 10. The labyrinth seal 114 is attached to impeller top plate 106 by tabs 118. Impeller vanes 110 are disposed between impeller top plate 106 and impeller bottom plate 108. Impeller vanes 110 are critical to the ability of blower assembly C to provide the required pressures for providing invasive ventilatory support. Impeller vanes 110 include first impeller vane end 120, which is disposed near the center of impeller port 112. The spacing between the respective impellers define centrifugal air passageways 122 that terminate at the distal impeller end 124. Accordingly, in operation, air is received through impeller port 112 and is manipulated by impeller vanes 110 and induced with centrifugal force and passed outward from the impeller to be received by the next stator.

Figure 11:
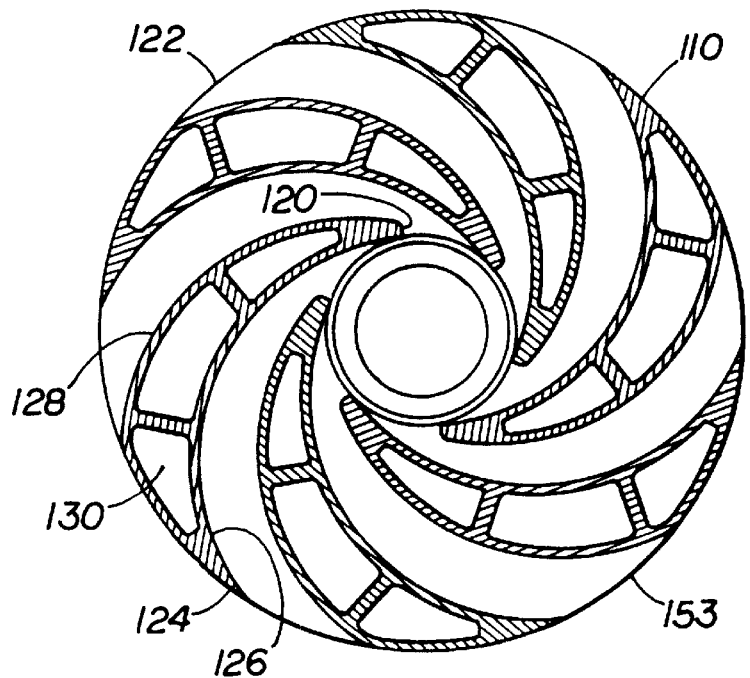
FIG. 11 is a cross-sectional view of an impeller taken along line 11—11 of FIG. 10.
Figure 12:
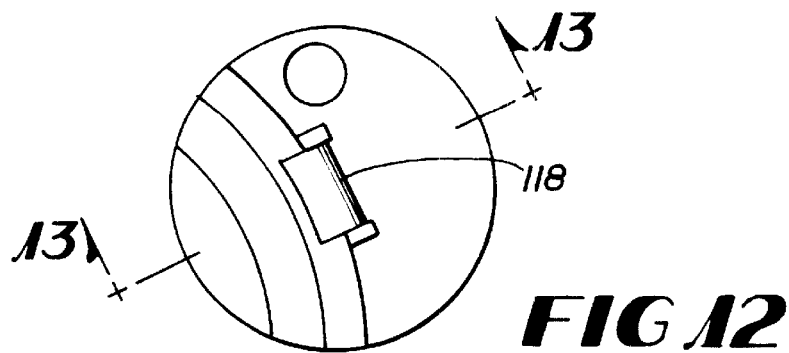
FIG. 12 is a detailed view of a sealing ring according to the present invention.
Figure 14:
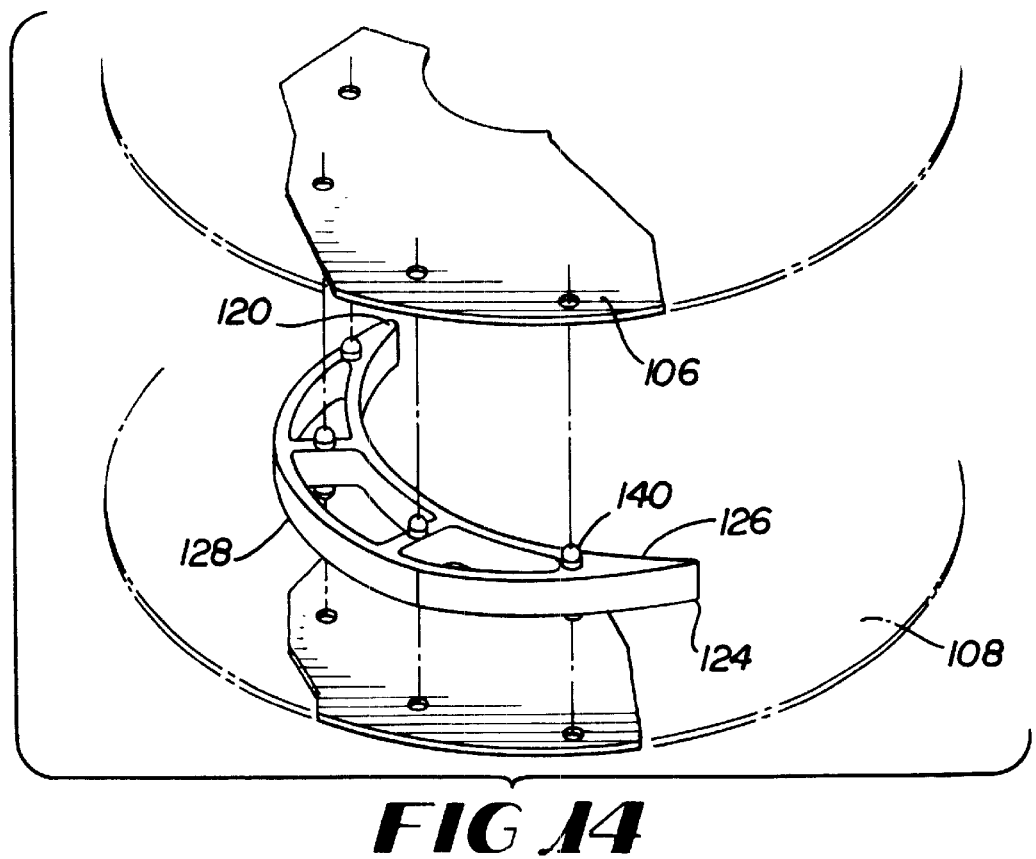
FIG. 14 illustrates a partial exploded view of an impeller vein attached to a lower and upper plate according to the present invention.
Figure 15:
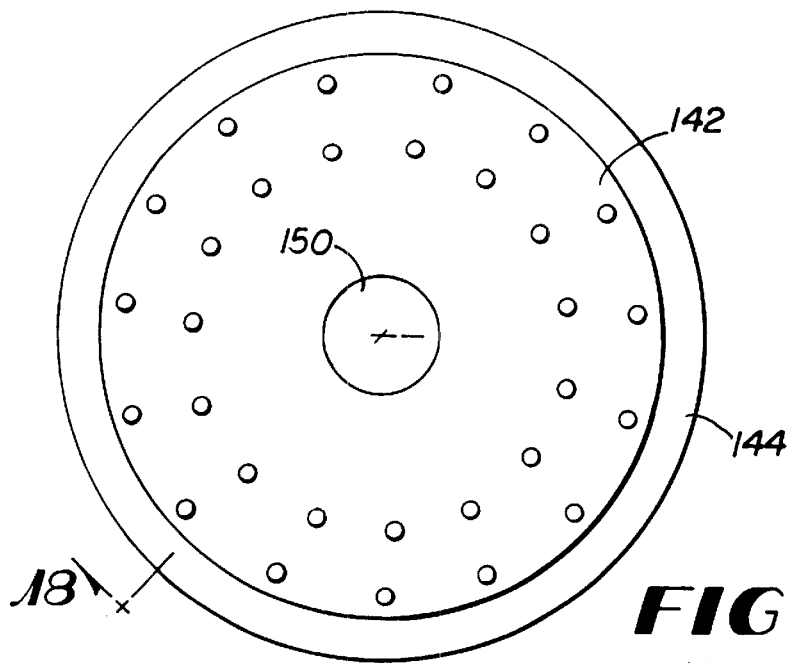
FIG. 15 is a top view of a stator according to the present invention.
Figure 16:
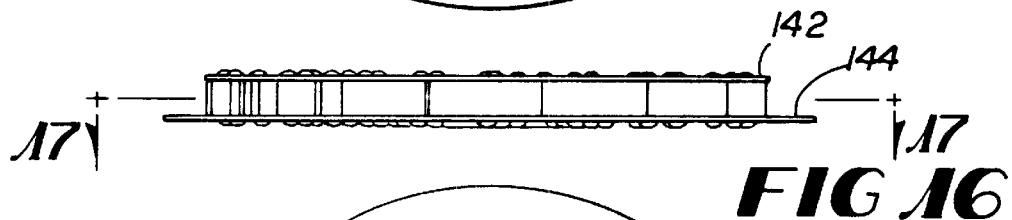
FIG. 16 is a side view of a stator according to the present invention.
Figure 17:
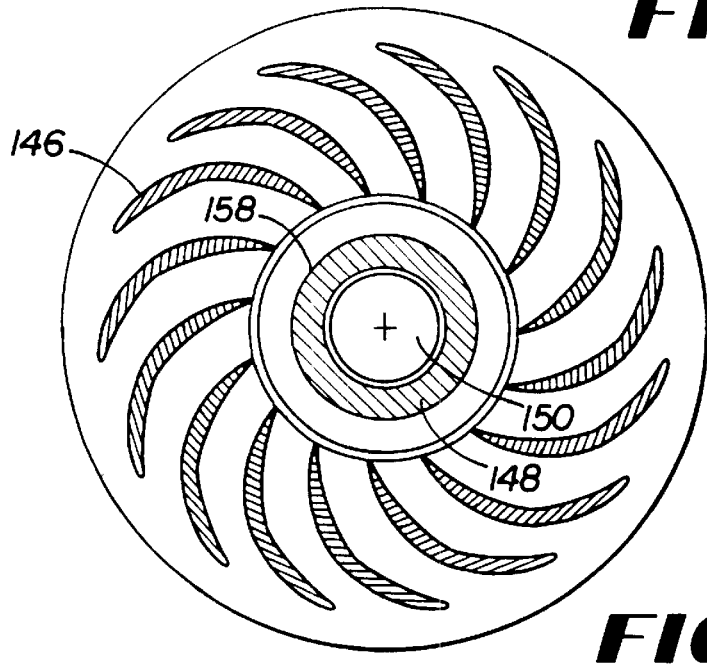
FIG. 17 is a cross-sectional view of a stator along line 17—17 of FIG. 16.
Figure 18:
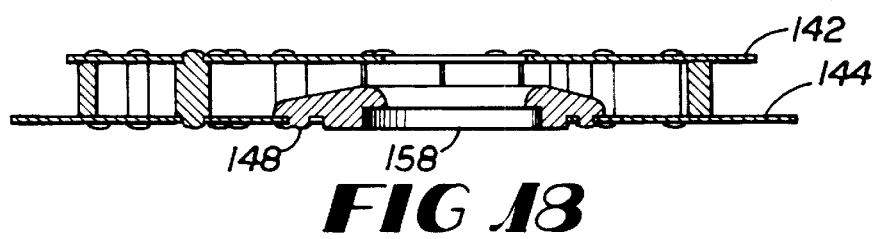
FIG. 18 is a cross-sectional view of the stator taken along line 18—18 in FIG. 15.
Figure 20:
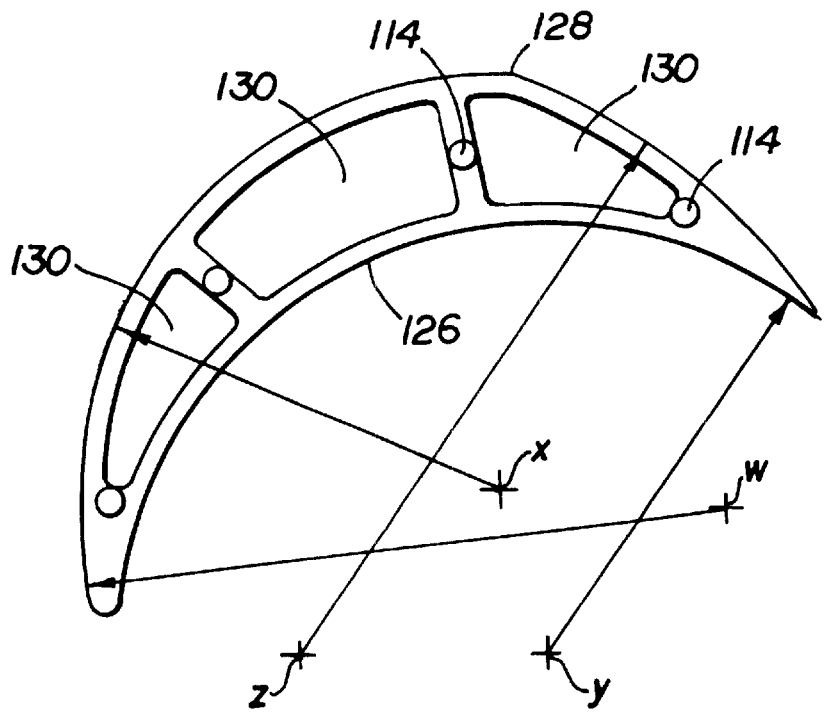
FIG. 20 is a view of an impeller blade according to the present invention.

As shown in FIGS. 11 and 20, in the preferred embodiment, impeller vanes 110 have an arcuate front surface 126 and respective arcuate back surface 128. Arcuate front surface 126 and arcuate back surface 128 are offset from one another to define an internal vane cavity 130. The hollow nature of the internal vanes enables the vanes to be lightweight while still imparting centrifugal force to the air. The impeller vanes have an internal radius preferably of forty three point ninety seven millimeters from point x and an internal radius preferably of sixty three point ninety eight millimeters as measured from point y. A lateral distance between points x and y is preferably eighteen point fifty five millimeters. Additionally, impeller vanes have an external radius preferably of sixty three point five millimeters from point z and a second external radius preferably of sixty six point fourteen millimeters from point w. The lateral distance between points z and w is preferably twenty five point fifty nine millimeters with a longitudinal distance of approximately thirteen point ninety eight millimeters. Both internal and outer edges are smooth. Tabs 140 eject upwards and downward from the respective vanes, as shown in FIG. 14, for attaching the vane with impeller top plate 106 and impeller bottom plate 108.

FIGS. 15, 16, 17, 18 and 21 illustrate stators 80 and 82. Stators 80 and 82 each include stator top plate 142 and stator bottom plate 144. Stator vanes 146 are disposed between stator top plate 142 and stator bottom plate 144. Stator air inlet passage 150 is disposed within stator top plate 142. An inducer 148 is disposed within stator bottom plate 144 and defines stator air exit port 158. As shown in FIG. 13, labyrinth seal 114 of the respective impellers matingly fit within stator air exit port 158 as defined by inducer 148. In this configuration, air flows through stator air inlet passage 150 and is compressed by stator vanes 146. The compressed air is then passed through stator air export 158 to the next impeller.

Figure 21:
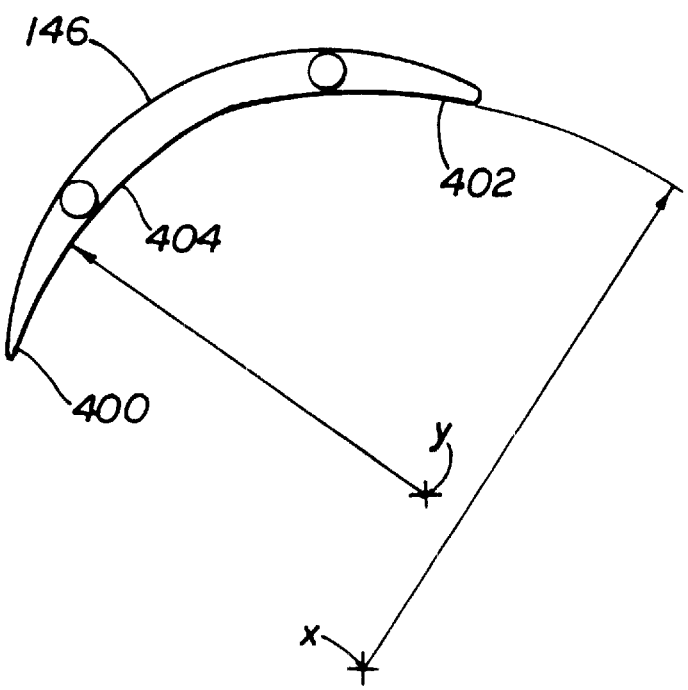
FIG. 21 is a view of a stator blade according to the present invention.

The configuration of stator vanes 146 is also critical to the invention. As shown in FIG. 21, stator vane 146 includes an interior portion 400 having a first curved surface 402 and a second curved surface 404. First curved surface 402 has a curvature radius of approximately forty nine point five millimeters as measured from point x. The second curved surface has a curvature radius of approximately twelve point seven millimeters as measured from point y. The lateral distance between point x and y is approximately six point four millimeters and the longitudinal distance is approximately thirty six point two millimeters.

It is critical that blower assembly C be able to supply sufficient air pressure for providing adequate invasive ventilatory assistance. In a preferred embodiment, blower assembly C provides air at a pressure of one hundred and five centimeters of $H_2O$ at two hundred liters per minute at blower air outlet 72.

With reference to FIGS. 7 through 18, in operation, air is drawn through central air port 68 to first impeller 74. Air is drawn into impeller port 112 and is charged with centrifugal energy due to the spinning rotation of the impeller vane. The charged air exits the first impeller 74 at impeller exit 153. The energized air is captured within first air chamber assembly 94 as defined by stator spaces 96 and 98 and directed interiorly to stator air inlet passage 150 where the air is then compressed and is drawn to the center of first stator 80 towards the inducer 148. Once compressed, the air passes through stator air exit port 158 and is directed by the curved profile of first impeller spacer 90 towards the interior of second impeller 76. The air is subsequently reenergized through centrifugal force of the revolving second impeller 76 and is directed outward through impeller exit 153 towards second air chamber assembly 95 as defined by second stator spacers 100 and 102 and redirected to second stator 92. The air is introduced to stator air inlet passage 150 of second stator 92 subsequently further pressurizing the air by passage between stator vanes 146. The pressurized air is subsequently directed towards second impeller spacer 92 through inducer 148 to impeller port 112 of third impeller 78. The air is further energized by the centrifugal rotation of the third impeller 78 and is directed against third stator spacer 104 and subsequently discharged to blower diffuser 103 through blower air outlet 72 and respective tubing.

An essential feature of the blower assembly C is that impeller vanes 110, stator vanes 146 and inducer 148 are made from polyetherimide, which are bio-compatible materials. Also the impeller top plate 106, impeller bottom plate 108, stator top plate 142, and stator bottom plate 144 and stator spacers 96, 98, 100, 102 and 104 are made from anodized aluminum which is also bio-compatible. The bio-compatible nature of the blower components enables air to be drawn from the environment and presented to the patient without being filtered upon exit from the blower. The elimination of a filter system eliminates any pressure drops which would be created by the existence of such a filter. Accordingly, the blower is efficient and provides the required pressures needed for invasive ventilation.

As shown in FIGS. 22 through 35, a critical feature of ventilator system A is the ability to provide invasive and non-invasive ventilation. Graphical user interface 31 located on front face of ventilator 10 enables the operator to control the operation of ventilator A. For invasive ventilation, ventilator A is designed to be operated in various volume ventilatory modes and pressure ventilatory modes. Additionally, ventilator A is designed to operate in a non-invasive mode. FIG. 22 illustrates the preferred operational parameters of ventilator system A in both invasive and non-invasive ventilatory modes.

Figure 23:
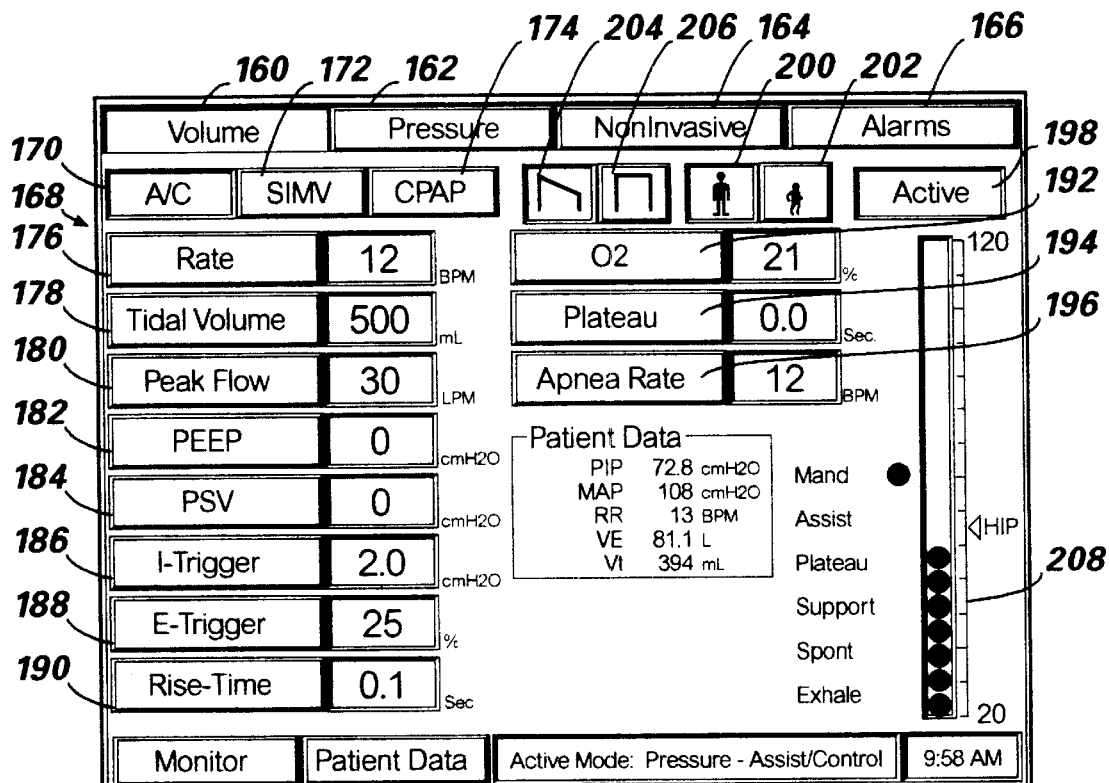
FIG. 23 is a view of a graphical user interface used in an invasive/non-invasive ventilator according to the present invention illustrating the user interface during the volume ventilation mode of invasive ventilation.

FIG. 23 illustrates graphical user interface 31. Graphical user interface 31 includes a plurality of buttons for selecting the desired mode of operation. In the preferred embodiment, graphical user interface 31 includes a volume ventilation button 160, pressure ventilation button 162, non-invasive ventilation button 164, and alarm button 166. In the preferred embodiment, graphical user interface has an infrared touch screen that allows the operator to select and display the ventilator settings. When a particular button is touched, that button is activated. It is to be understood, however, that other types of user interface techniques, such as cursors, keyboard, and stylus, can be used to activate selected portions of the interface screen.

As illustrated in FIG. 23, the volume ventilation button 160 is activated to view the settings for volume ventilation which is volume ventilation display 168. The volume ventilation display 168 as shown in FIG. 23 displays the various parameters related to volume ventilation. In the illustrated embodiment, volume ventilation display 168 include: an A/C button 170, a SIMV button 172, and a CPAP button 174. The various parameters utilized for controlling the operation of ventilation A relating to volume ventilation includes breath rate button 176, tidal volume button 178, peak flow button 180, PEEP button 182, PSV button 184, I-trigger button 186, E-trigger button 188 and rise time button 190. The current active state of ventilation is displayed by state button 191. As shown in FIG. 23, the active state is volume assist/control.

The A/C button is used in conjunction with the I-trigger sensitivity setting to deliver mandatory or assisted breaths. If only machine-triggered mandatory breaths are desired, the operator can set the mode to assist and set I-trigger to the maximum setting. If assisted breaths are desired, the operator can set the mode to A/C and I-trigger to match the patient's respiratory demand. SIMV allows the operator to select a mandatory breath rate. This mode will allow patient-initiated, spontaneous breaths. Mandatory volume-controlled ventilation is also available in this mode. Pressure support ventilation is also allowed in this mode. CPAP delivers spontaneous breaths.

Rate button 176 determines the number of mandatory breaths per minute for mandatory breaths. This setting is used to determine the frequency of mandatory breaths. In a preferred embodiment acceptable inputs for the breath rate are one to eighty breaths per minute. Tidal volume button 178 controls the volume of gas delivered to the patient during a mandatory, volume-controlled breath. Acceptable ranges are fifty milliliters to two point five liters. Peak flow button 180 determines the maximum rate of gas volume delivery from the ventilator during mandatory, volume-based breaths. In the preferred embodiment, the setting ranges extend from three to one hundred and forty liters per minute. PEEP button 182 is the operator-selected, positive pressure maintained in the circuit during the expiratory portion of a breath cycle. In the preferred embodiment, the settings may range between zero to thirty five centimeters $H_2O$. PSV button 184 provides positive pressure to the patient's airway during a spontaneous breath. In the preferred embodiment, the settings range between zero to one hundred centimeters $H_2O$. I-trigger button 186 is the level of pressure or flow required to initiate an inspiration. E-trigger button 188 is a percent of peak inspiratory flow that, when reached, causes the system to transition from inhalation to exhalation. Rise time button 190 is used to vary the rate of change and the amount of pressure delivered during inspiration during pressure support breath delivery.

Figure 24:
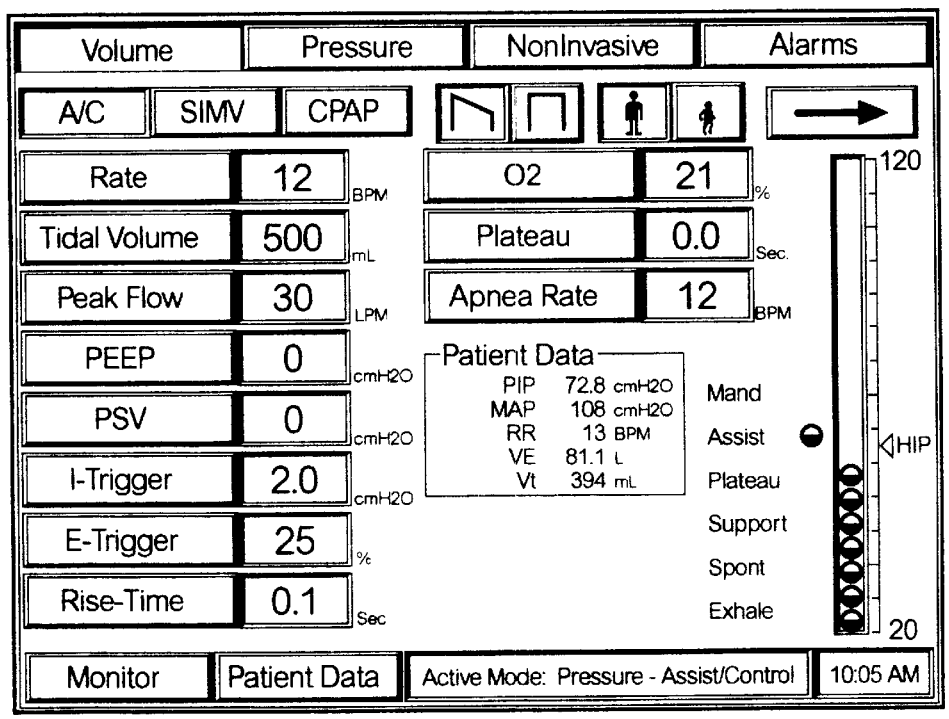
FIG. 24 is a view of a graphical user interface used in an invasive/non-invasive ventilator according to the present invention illustrating the user interface for the volume ventilation mode of invasive ventilation during pressure ventilation.
Figure 26:
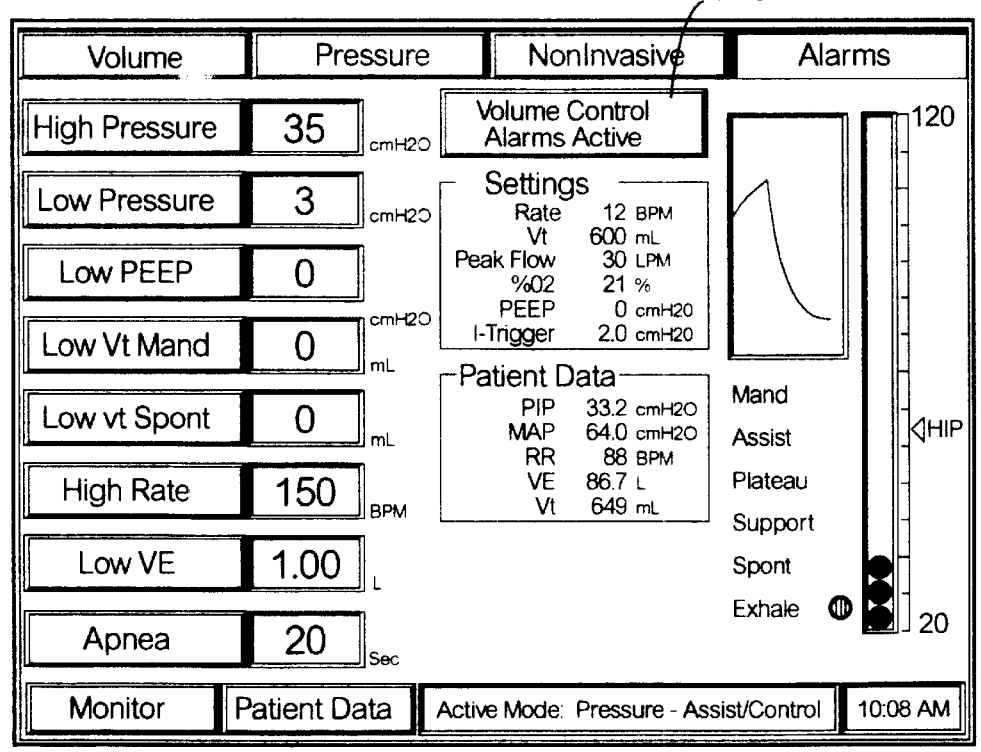
FIG. 26 is a view of a graphical user interface used in an invasive/non-invasive ventilator according to the present invention illustrating the user interface for setting alarms in a volume ventilation mode.

Additionally an $O_2$ button 192 enables the operator to determine the percentage of oxygen in the delivered gas. A plateau button 194 determines the time interval for which pressure will be maintained during inspiratory phase of a mandatory breath following cessation of flow from the ventilator. An apnea rate button 196 determines respiratory rate of breaths delivered during apnea ventilation. Also, a start-active button 198 activates the parameters displayed. Accordingly, when switching between modes of operation, this button must also be depressed to prevent accidental switching between modes of operation. Additionally, an adult button 200 and child button 202 are provided to select between a pediatric and adult application, which will adjust the breath delivery algorithm accordingly. Flow pattern buttons 204 and 206 show the gas flow pattern of volume controlled mandatory breaths. The related inspiratory to expiratory ratio of inspiratory time will be altered depending on the selected waveform. As shown in FIG. 24, if volume ventilation is selected from a previous pressure assist mode, the various parameters previously selected for volume ventilation will be displayed, however, volume ventilation mode is inactive as evidenced by the start button becoming an arrow. If the operator desires to make the volume ventilation active, activation button 209 as shown in FIG. 26 will need to be activated. Also illustrated in FIG. 23, a pressure manometer 208 is located on the screen with a high inspiratory pressure alarm mark noted on the manometer. The manometer is always visible to an operator.

Figure 25:
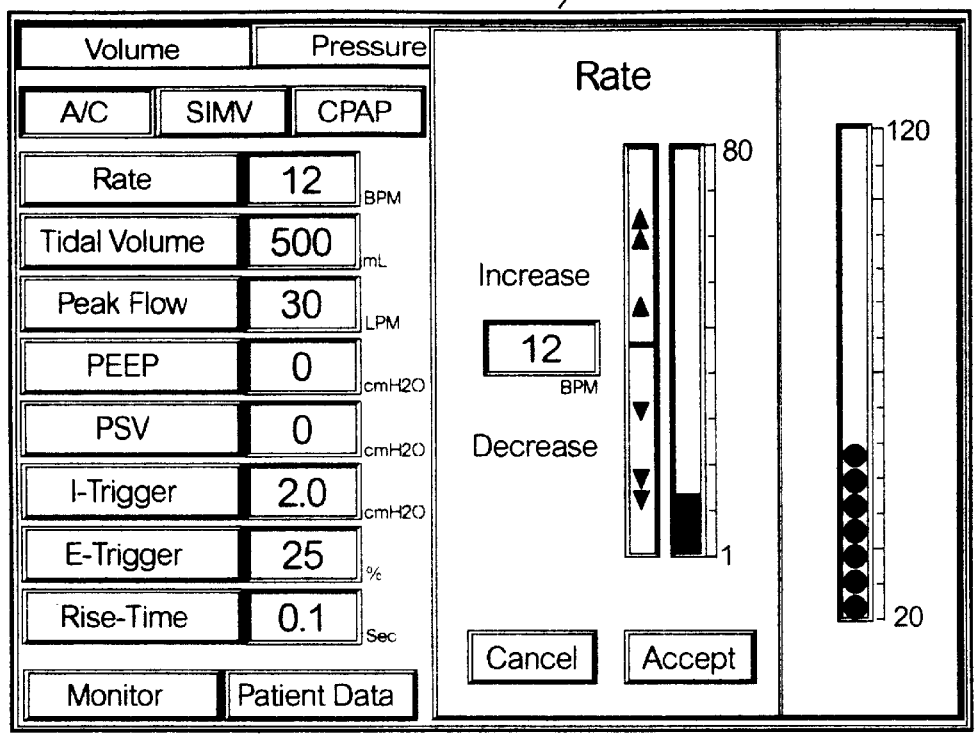
FIG. 25 is a view of a graphical user interface used in an invasive/non-invasive ventilator according to the present invention illustrating the user interface for manipulating certain parameters during volume ventilation mode.

As shown in FIG. 25, the manipulation of particular parameters is achieved by selecting the particular parameter to be manipulated and a pop-up window 207 of that particular parameter is displayed on the graphical user interface.

For instance, to manipulate the rate parameter in volume ventilation, the rate button is depressed and the pop-up window for the rate parameter is displayed. From this pop-up window, the rate may be either increased or decreased within the established machine limits. The operator can then accept or cancel the change for the given parameter by pressing the appropriate button.

Figure 28:
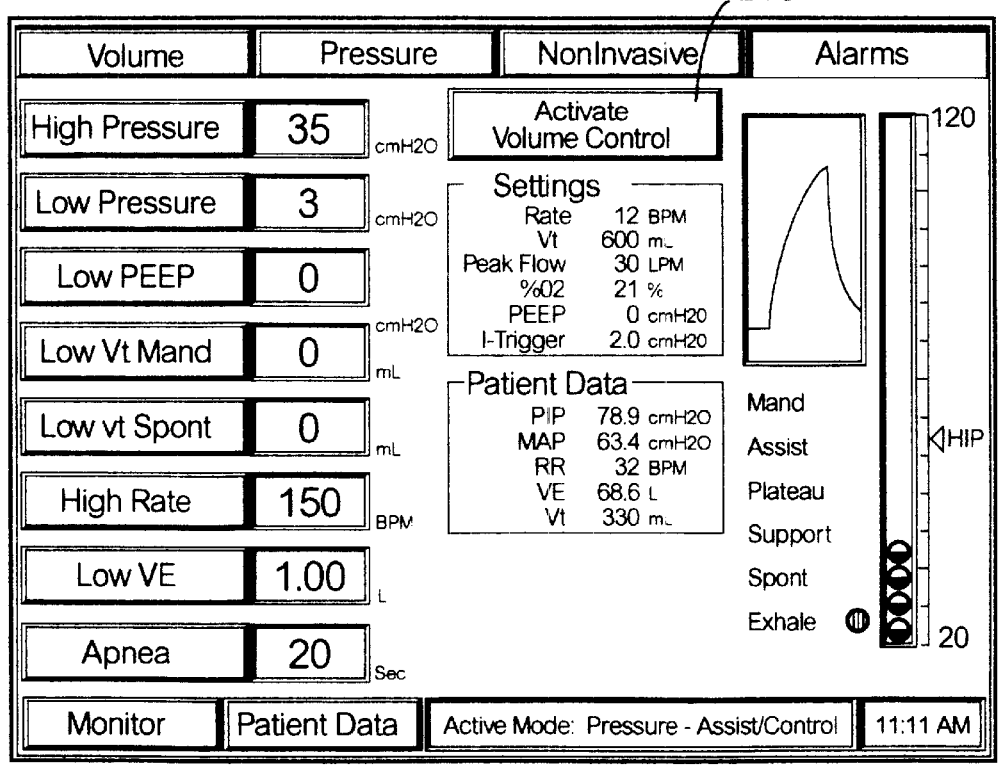
FIG. 28 is a view of a graphical user interface used in an invasive/non-invasive ventilator according to the present invention illustrating the user interface for setting the volume ventilation control alarms while in pressure ventilation mode.

FIG. 26 illustrates the alarms related to volume ventilation. In one embodiment of the present invention, these alarms include, for example, high inspiratory pressure, low inspiratory pressure, low PEEP, low mandatory exhaled tidal volume, low spontaneous tidal volume, high respiratory rate, low expiratory minute volume and apnea interval occurring. Each of these alarms have a respective button for manipulating the various alarm parameters. Also, the current settings are displayed along with updated patient data. FIG. 28 illustrates the volume alarm parameters when volume ventilation is not active. Accordingly, all alarm modes for each respective modes of operation may be used at any time without affecting the particular mode of operation in which ventilator A is currently operating. Activation button 209 is utilized for activating the volume control mode.

Accordingly, in operation, if an operator desires to operate ventilator 10 in a volume control mode, the operator will first select volume ventilation button 160 which then displays volume ventilation display 168. At this time, any parameters shown by volume ventilation display 168 may be manipulated. The operator then subsequently activates alarm button 166 to enter into the alarm display for volume ventilation. Upon verifying the accuracy of the various alarm buttons, the operator will then activate activation button 209 and the machine will then enter into volume ventilation mode. As shown in FIG. 26, if the active mode is already volume control ventilation, then activate button 209 will merely indicate that the volume control alarms are active.

Figure 27:
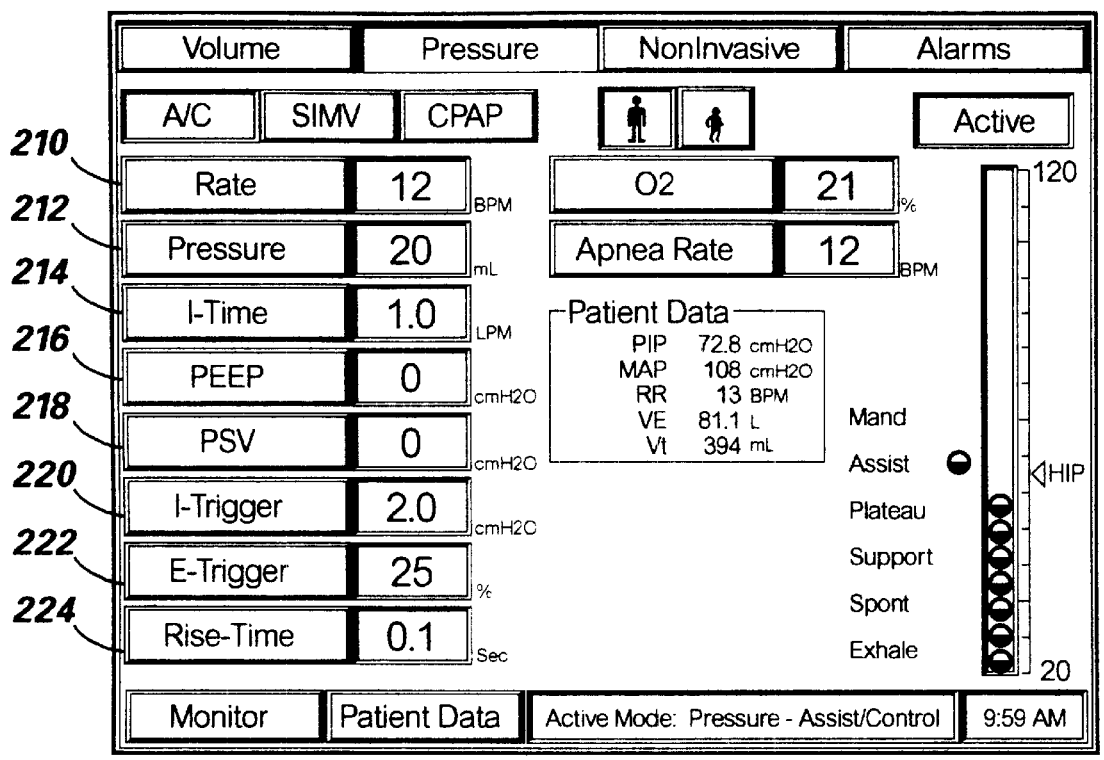
FIG. 27 is a view of a graphical user interface used in an invasive/non-invasive ventilator according to the present invention illustrating the user interface during the pressure ventilation mode of invasive ventilation.

FIG. 27 illustrates graphical user interface 31 when pressure ventilation mode is active. In the pressure ventilation mode, various modes of pressure ventilation may be provided by ventilator A including assist/control pressure ventilation, SIMV pressure ventilation and CPAP. In the illustrated embodiment, the various buttons for pressure ventilation include: the breath rate button 210, pressure button 212, I-time button 214, PEEP button 216, PSV button 218, I-trigger button 220, E-trigger button 222, and rise time button 224.

Pressure button 212 determines the pressure target to be delivered during mandatory or assist breaths. Preferable setting ranges extend from zero to one hundred centimeters $H_2O$. I-time button 214 setting is used to vary the amount of time spent in the inspiratory phase of the breath cycle and the preferred ranges vary from point one to nine point nine seconds. PSV button 218 provides positive pressure to the patient's airway during a spontaneous breath and the preferable settings range from zero to one hundred centimeters $H_2O$.

Figure 29:
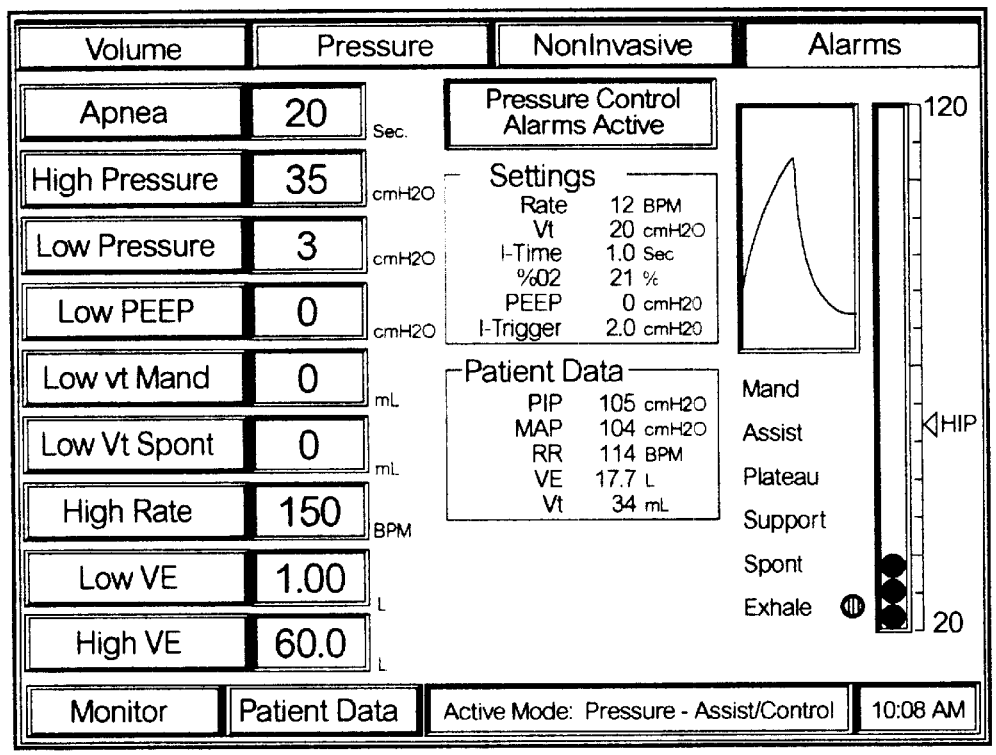
FIG. 29 is a view of a graphical user interface used in an invasive/non-invasive ventilator according to the present invention illustrating the user interface for setting alarms in the pressure ventilation mode.

FIG. 29 illustrates the alarms associated with pressure ventilation. In the illustrated embodiment, these alarms include: apnea interval, high pressure, low pressure, low PEEP, low tidal volume on a mandatory exhaled tidal volume and a low range limit on spontaneous exhaled tidal volume, high exhaled minute volume and low exhaled minute volume. Each of these alarms have a related button enabling the operator to select the alarm condition parameter.

Figure 30:
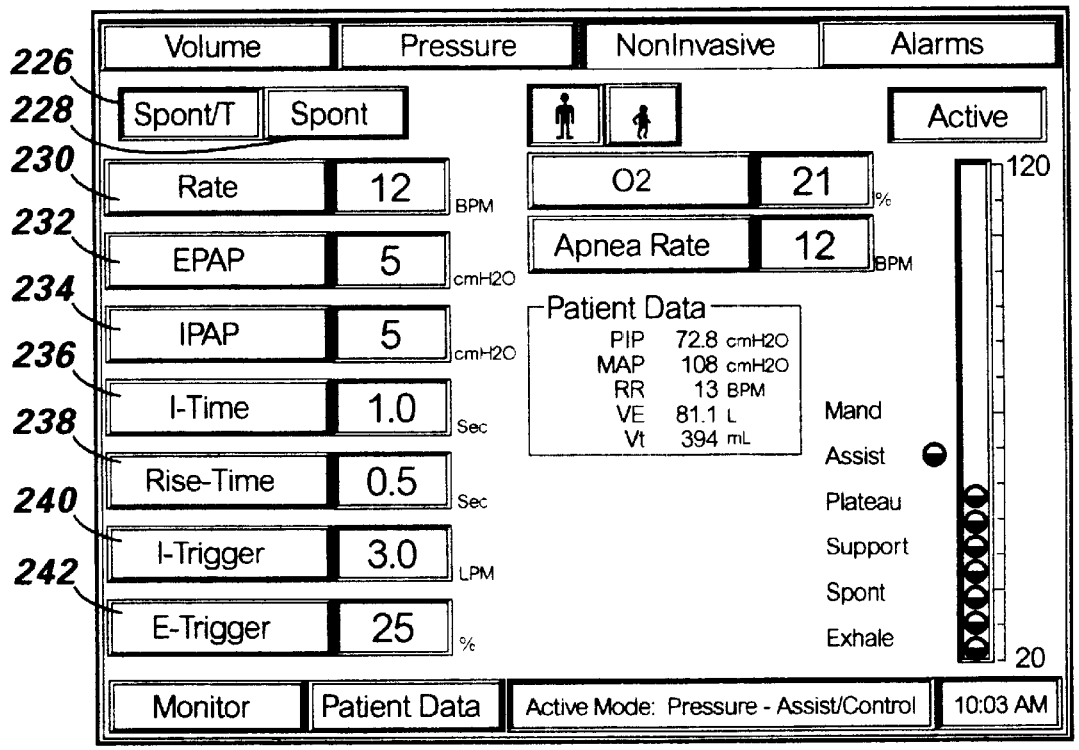
FIG. 30 is a view of a graphical user interface used in an invasive/non-invasive ventilator according to the present invention illustrating the user interface in a non-invasive mode.

FIG. 30 illustrates graphical user interface 31 with the non-invasive ventilation mode active. Buttons present in the illustrated embodiment of the non-invasive ventilation mode include spont-T button 226, spont button 228, breath rate button 230, EPAP button 232, IPAP button 234, I-time button 236, rise time button 238, I-trigger button 240, and E-trigger button 242. Spont-T mode delivers inspiratory/ expiratory pressures based on the operator selected IPAP and EPAP pressure setting. Breath delivery is determined by patient effort and respiratory demand, as well as operator selected rate setting. The breath cycle for mandatory breaths is determined by I-time setting. Spont mode delivers and maintains the inspiratory and expiratory pressure in synchrony with patient's triggering of inspiratory and expiratory efforts. Pressure breath delivery is determined by IPAP, EPAP and the rise time settings. EPAP functions in the same manner as PEEP/CPAP settings and the pressure and volume ventilation modes. However, in a non-invasive mode of operation, the settings may only range from two to twenty five centimeters $H_2O$. IPAP functions in a manner similar to that of pressure support ventilation but is only available in a non-invasive mode and the settings may only range from two to thirty five centimeters $H_2O$.

Figure 31:
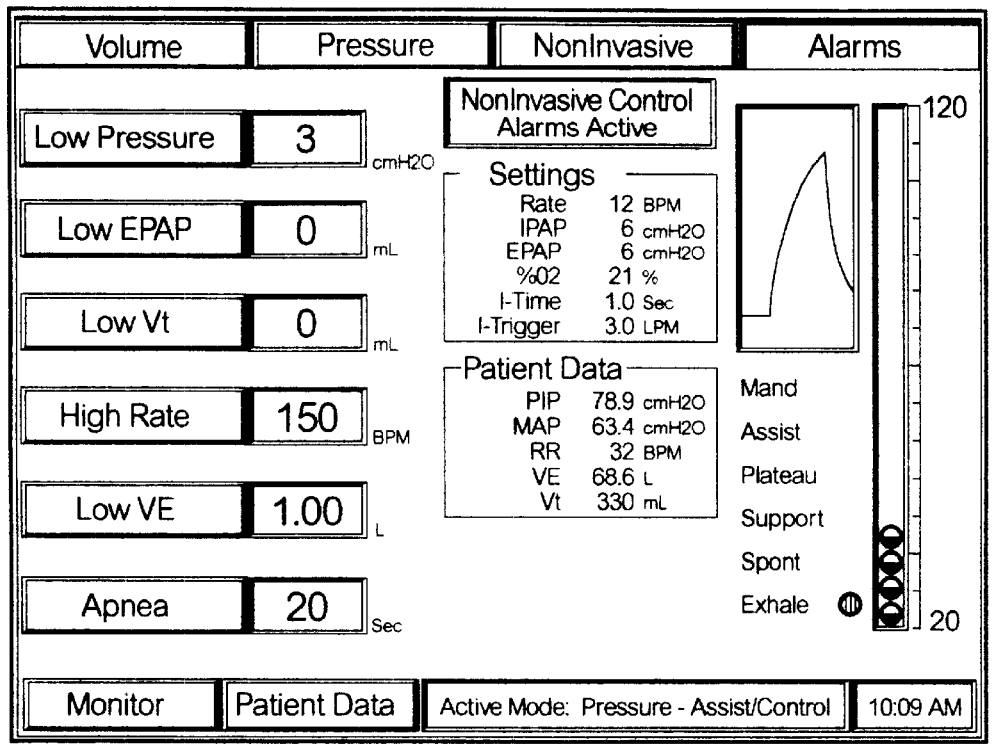
FIG. 31 is a view of a graphical user interface used in an invasive/non-invasive ventilator according to the present invention illustrating the user interface in setting alarms for non-invasive ventilation.

FIG. 31 illustrates the alarm settings in a non-invasive ventilation mode. The alarm settings in the illustrated embodiment include: low pressure, low EPAP, low exhaled tidal volume, high breath rate, low exhaled minute volume, and apnea interval. In a preferred embodiment, no high pressure alarm is provided and is automatically set in the preferred embodiment to be ten centimeters $H_2O$ higher than the previously designated IPAP pressure.

Figure 32:
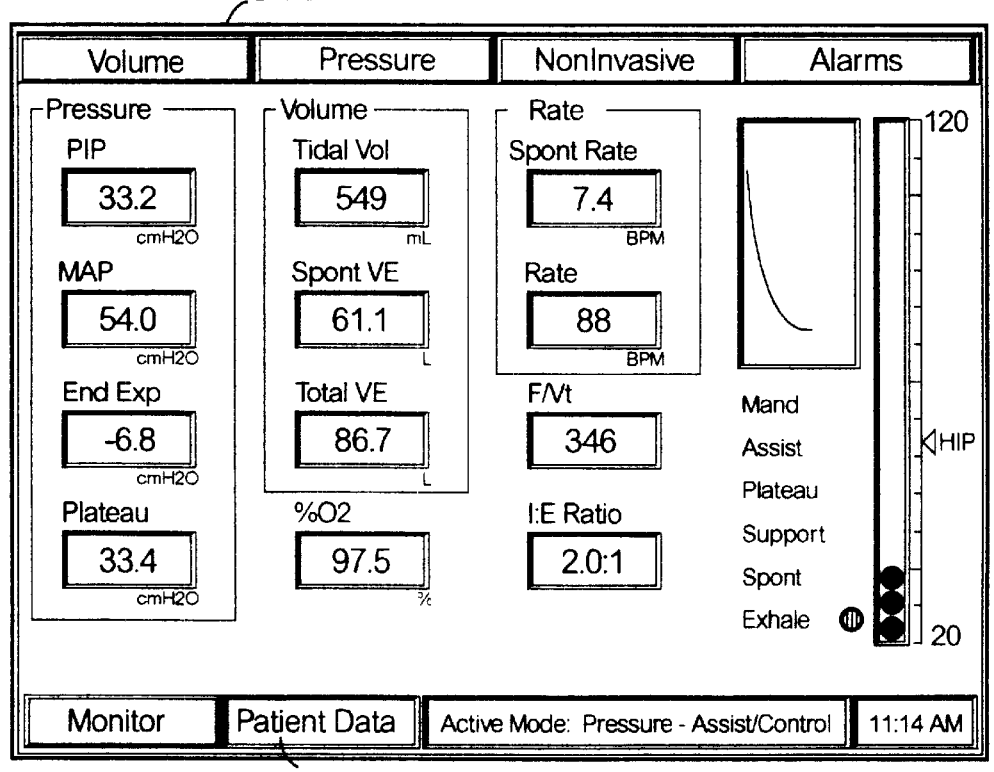
FIG. 32 is a view of a graphical user interface used in an invasive/non-invasive ventilator according to the present invention illustrating the use of the interface as a display for displaying the patient data.

As shown in FIG. 32, a patient data screen 244 is also included in graphical interface 31. Monitored patient data is displayed when patient data button 211 is pressed. Various parameters which may be displayed include exhaled minute volume, exhaled tidal volume, spontaneous minute volume, rapid shallow breathing index, inspiratory/expiratory ratio, peak inhalation pressure, plateau pressure, mean airway pressure, delivered oxygen concentration, total respiratory rate, spontaneous respiratory rate, and end inhalation pressure. In a preferred embodiment, the rapid shallow breathing index only appears during spontaneous breathing modes of operation.

Figure 33:
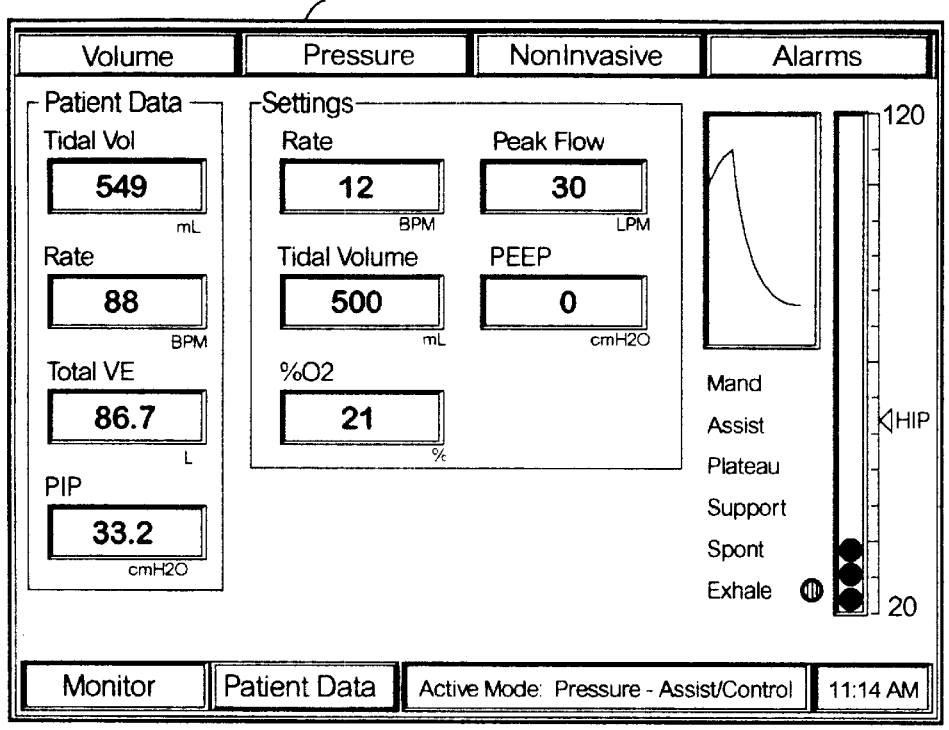
FIG. 33 is a view of a graphical user interface used in an invasive/non-invasive ventilator according to the present invention illustrating the use of the interface as a monitor for monitoring the patient during volume ventilation.
Figure 34:
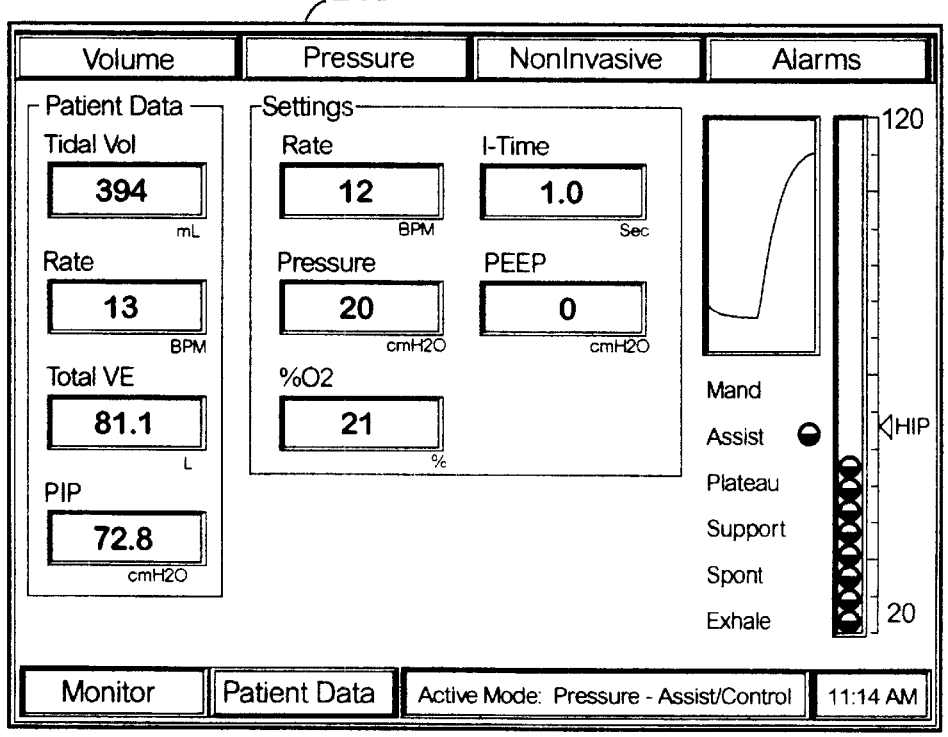
FIG. 34 is a view of a graphical user interface used in an invasive/non-invasive ventilator according to the present invention illustrating the use of the interface as a monitor for monitoring the patient during pressure ventilation.
Figure 35:
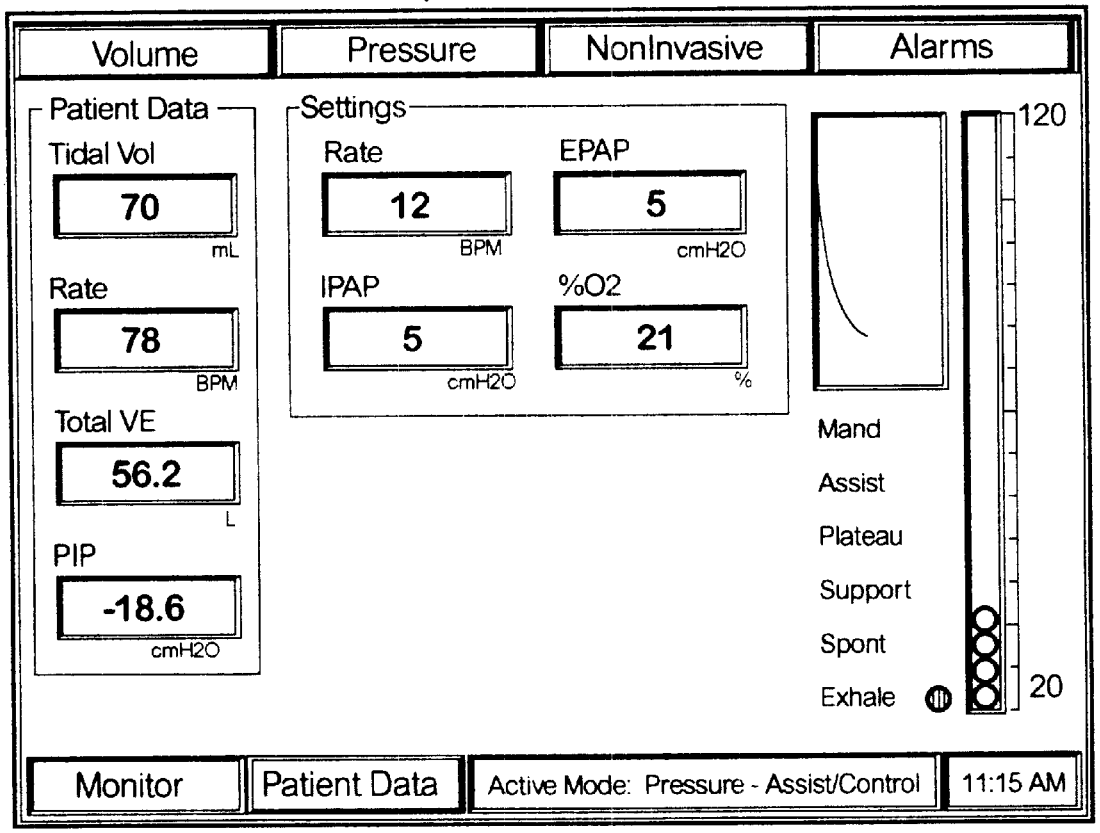
FIG. 35 is a view of a graphical user interface used in an invasive/non-invasive ventilator according to the present invention illustrating the use of the interface as a monitor for monitoring the patient during non-invasive ventilation.

As shown in FIGS. 33, 34, and 35, monitors 246 may be provided for showing some attributes of patient data and also of various settings in that particular mode of activation. For instance, in the volume ventilation mode, the primary setting displayed will be tidal volume, while in pressure ventilation mode, the pressures will be displayed and non-invasive ventilation EPAP and IPAP will be displayed. Each of these respective settings are critical for their respective modes of operation.

Also as shown in FIGS. 23 through 35, pressure manometer 208 is consistently shown in the right hand corner of all screens. An indicator for high inspiratory pressure limit is displayed next to the pressure manometer. Touching the HIP indicator will open a dialog window for setting the high inspiratory pressure limit. The manometer consists of symbols indicating the respective pressure. These symbols also function as a breath type indicator which is updated at the start of each inspiration. In the illustrated embodiment, five different symbols exist. A first breath type signal is shown if the breath type is mandatory and is triggered either by the operator or ventilator. A second breath type signal is shown if the breath type is mandatory and is initiated by the patient thereby indicating an assisted breath. A third breath type signal is shown if the breath type is spontaneous and pressure supported and pressure support is not enable. A fourth breath type signal is shown if the breath is spontaneous and pressure support ventilation is active and a spontaneous breath is triggered. A fifth breath type signal is shown during exhalation. These symbols assist an operator who is not attending the machine from visually monitoring the machine from afar to ascertain how the patient is breathing on the ventilator.

For power supply, the ventilator is designed to accept a variety of power sources and also includes an internal battery supply.

Accordingly, in operation, the operator utilizes the graphical user interface for manipulating the operation of ventilator A into either an invasive or non-invasive mode of operation. For invasive ventilatory assistance, the operator can select either volume or pressure ventilation. When the operator selects the desired ventilatory assistance, only those controlled parameters utilized for that particular ventilatory mode of operation are displayed by the graphical user interface. With the appropriate controls displayed, the operator may then input the desired controlled parameters for that particular mode of ventilatory assistance. Control parameters for that particular mode of ventilation are stored in memory and utilized by control algorithms for controlling the operation of the ventilator and the respective valves. While certain parameters may be similar in other modes of ventilatory assistance, such as breathing rate, these parameters are distinct between the respective ventilatory modes. This is also true for the respective alarms.

Accordingly, as the patient is being weaned from the ventilator, ventilator A may be manipulated by the operator to select the different styles of invasive ventilation and then subsequently utilize the non-invasive mode of operation for further weaning the patient after the endotracheal tube has been removed.

Thus, it may be seen, that an advantageous technique for providing ventilatory assistance to a patient is provided according to the present invention. By utilizing a single ventilatory system, an operator may provide both invasive and non-invasive ventilation support to a patient as the patient improves in their health. By providing a single interface and only providing those specific parameters to that mode of operation, errors in providing ventilatory support may be reduced. Also, only those parameters relevant to that specific mode of operation are presented to the operator reducing the confusion that may be had if all possible controls were presented to the operator at the same time. Additionally by providing a blower based ventilatory system, ventilatory assistance may be provided at facilities which are not constructed with fixed air and oxygen supplies.

It thus will be appreciated that the objects of this invention have been fully and effectively accomplished. It will be realized, however, that the foregoing preferred specific embodiment has been shown and described for the purpose of this invention and is subject to change without departure from such principles. Therefore, this invention includes all modifications encompassed within the spirit and scope of the following claims.

What is claimed is:

1. A ventilator system for providing ventilatory support to a patient, said ventilator system comprising:
   a gas flow generator for providing a flow of gas to a patient;
   a conduit for delivery of said gas flow to an airway of a patient;
   at least a first valve for regulating delivery of gas from said gas flow generator to said conduit;
   a controller for controlling delivery of said gas flow to a patient;
   a first set of operational parameters for directing sad controller to control delivery of gas to a patient in an invasive ventilation mode;
   a second set of operational parameters for directing said controller to control delivery of gas to a patient in a non-invasive ventilation mode;
   a selector for selecting either said first or said second set of parameters to direct said ventilator system to provide either invasive or non-invasive ventilatory support to a patient; and
   a display for displaying said first and said second set of parameters said first and said second set of parameters nor being simultaneously displayed by said display.

2. The ventilator system of claim 1, wherein said first set of parameters include at least one parameter relating to volume ventilation selected from the group consisting of breathing rate, tidal volume, and peak flow.

3. The ventilator system of claim 1, wherein said first set of parameters include parameters relating to volume ventilation in delivering assisted ventilatory support, control ventilatory support, intermittent ventilatory support and continuous positive airway pressure support.

4. The ventilator system of claim 1, wherein said first set of parameters include at least one parameter relating to pressure ventilation selected from the group consisting of breathing rate, pressure and I-time.

5. The ventilator system of claim 1, wherein said first set of parameters include parameters relating to pressure ventilation in delivering assisted ventilatory support, control ventilatory support, intermittent ventilatory support and continuous positive airway pressure support.

6. The ventilator system of claim 1, wherein said second set of parameters relating to the delivery of non-invasive ventilation include at least one parameter selected from the group consisting of breathing rate, inhalation positive airway pressure and expiratory positive airway pressure.

7. The ventilator system of claim 1, wherein a third set of parameters relating to the delivery of invasive ventilation, said first set of parameters corresponding to volume ventilation and said third set of parameters relating to pressure ventilation.

8. The ventilator system of claim 1, wherein said selector includes an infrared touch screen.

9. The ventilator system of claim 1, including a manometer displayed by said display.

10. The ventilator system of claim 1, including a breath parameter displayed by said display, said breath parameter corresponding to a type of breath administered by said ventilator system.

11. The ventilator system of claim 1, wherein said gas flow generator comprises:
    at least two stators having stator vanes, said stator vanes big bio-compatible; and
    at least two impellers having impeller vanes, said impeller vanes being bio-compatible.

12. The ventilator system of claim 1, wherein said select comprises a graphical user interface having an activation area for activating either said invasive or noninvasive ventilatory support.

13. The ventilation system of claim 11 wherein said graphical user interface inches controls for modifying either said first or second set of operational parameters when displayed by said display.

14. The ventilator system of claim 1, wherein said gas flow generator comprises:

gas inlet for receiving said gas from an ambient environment;

a first impeller for imparting centrifugal force onto said gas;

a first stator for receiving said gas from said fist impeller and for pressurizing said gas;

a second impeller for receiving said gas from said first stator and for imparting centrifugal force onto said gas;

a first impeller spacer for directing said pressurized gas from said first stator to said second impeller;

a second stator for receiving said gas from said second impeller and for pressurizing said gas;

a third impeller for receiving said gas from said second stator and for imparting centrifugal force on to said gas;

a second impeller spacer for directing said gas from said second stator to said third impeller; and an outlet, wherein said gas is pressurized to at least one hundred and five centimeters $H_2O$ at a blower outlet.

15. The gas flow generator of claim 14, wherein said first, second and third impellers each include impeller vanes.

16. The gas flow generator of claim 15, wherein said impeller vanes have an interior side having a first curved surface of approximately sixty-three point nine millimeters when measured from a first reference point and a second curved surface of approximately forty three point nine millimeters when measured from a second reference point.

17. The gas flow generator of claim 15, wherein each impeller is circular and includes six impeller vanes spaced around the circumference of the respective impeller.

18. The gas flow generator of claim 15, wherein said impeller vanes have a first surface and a second surface which are offset defining internal cavities.

19. The gas flow generator of claim 14, wherein said first and second stators include stator vanes.

20. The gas flow generator of claim 19, wherein said stator vanes have a first interiorly curved surface of approximately forty-nine point five millimeters when measured from a first reference pint and a second interiorly curved surface of approximately twenty-seven point two millimeters when measured from a second reference point.

21. The gas flow generator of claim 19, wherein said stators are circular and each stator includes fifteen stator vanes disposed along the circumference of each respective stator.

22. A ventilator system for providing ventilatory support to a patient, said ventilator system comprising:

a blower having a blower outlet for providing gas to a patient;

a conduit in communication with said blower outlet for delivering said gas to a patient;

a controller for controlling delivery of said gas from said blower to a patient;

a first set of operational parameters corresponding to volume ventilation for delivering volume ventilation in an invasive ventilatory environment;

a second set of operational parameters corresponding to pressure ventilation for delivering volume ventilation in an invasive ventilatory environment;

a third set of operational parameters corresponding to non-invasive ventilation for delivering noninvasive ventilation in a non-invasive ventilatory environment;

a selector for selecting either said first, second or third operational parameters for delivering ventilatory support to the patient; and a display for displaying either said first, second or third operational parameters once selected;

a blower valve for controlling a flow of pressurized air from said blower outlet;

an oxygen supply system for intermixing oxygen with said pressurized gas;

oxygen valve for controlling a flow of oxygen to be delivered to a patient; and a first flow sensor for measuring flow of said pressurized gas from said blower and a second flow sensor for measuring flow of oxygen in said oxygen supply system, said controller controlling said blower valve and said oxygen valve based on flow values sensed by said first and second flow sensors for controlling an oxygen mix delivered to a patient.

23. The ventilator system of claim 22, wherein said blower provides at least one hundred and five centimeters of $H_2O$ of pressurized gas at said blower outlet at a flow rate of two hundred liters per minute.

24. The ventilator system of claim 22, including an exhalation passageway for communicating exhaled air from a patient to an ambient environment and an exhalation valve located in said exhalation passageway for controlling pressure within said expiratory passageway.

25. The ventilator system of claim 22 further including a plurality of alarms corresponding with said first, second and third operational parameters.

26. The ventilator system of claim 22, wherein said selector includes an infra-red touch screen.

27. The ventilator system of claim 22, including a manometer displayed by said display.

28. The ventilator system of claim 22, including a breath parameter displayed by said display, said breath parameter corresponding to a type of breath administered by said ventilator system.

29. The ventilator system of claim 22, including a blower valve for controlling a flow of pressurized air from said blower outlet.

* * * * *